(12) United States Patent
Lachenbruch et al.

(10) Patent No.: US 6,772,825 B2
(45) Date of Patent: Aug. 10, 2004

(54) HEAT EXCHANGE SUPPORT SURFACE

(76) Inventors: Charles A. Lachenbruch, 126 Linwood La., Summerville, SC (US) 29483; Roger B. Lachenbruch, 11 Natalie Cir., Petaluma, CA (US) 94952

( * ) Notice: Subject to any disclaimer, the term of this patent is extended or adjusted under 35 U.S.C. 154(b) by 18 days.

(21) Appl. No.: 10/287,317

(22) Filed: Nov. 4, 2002

(65) Prior Publication Data

US 2004/0084174 A1 May 6, 2004

(51) Int. Cl.[7] .................................................. F28F 7/00
(52) U.S. Cl. ........................... 165/46; 607/96; 607/108; 607/114; 5/421; 5/655.5
(58) Field of Search ............................... 165/46; 607/96, 607/108, 112, 114; 5/421, 655.5; 62/530

(56) References Cited

U.S. PATENT DOCUMENTS

| | | |
|---|---|---|
| 4,596,250 A | 6/1986 | Beisang, III et al. |
| 4,651,369 A | 3/1987 | Guldager |
| 4,671,267 A | 6/1987 | Stout |
| 4,699,134 A | 10/1987 | Samuelson |
| 4,708,812 A | 11/1987 | Hatfield |
| 4,807,696 A | 2/1989 | Colvin et al. |
| 4,911,232 A | 3/1990 | Colvin et al. |
| 4,964,402 A | 10/1990 | Grimm et al. |
| 4,999,867 A | 3/1991 | Toivio et al. |
| 5,010,608 A | 4/1991 | Barnett et al. |
| 5,033,136 A | 7/1991 | Elkins |
| 5,300,103 A | 4/1994 | Stempel et al. |
| 5,366,801 A | 11/1994 | Bryant et al. |
| 5,511,260 A | 4/1996 | Dinsmoor, III et al. |
| 5,586,346 A | 12/1996 | Stacy et al. |
| 5,722,482 A | 3/1998 | Buckley |
| 5,800,480 A | 9/1998 | Augustine et al. |
| 5,817,145 A | 10/1998 | Augustine et al. |
| 5,837,002 A * | 11/1998 | Augustine et al. ........... 607/104 |
| 5,890,245 A | 4/1999 | Klearman et al. |
| 5,926,884 A | 7/1999 | Biggie et al. |
| 5,964,723 A | 10/1999 | Augustine |
| 5,983,429 A | 11/1999 | Stacy et al. |
| 6,004,662 A | 12/1999 | Buckley |
| 6,010,528 A * | 1/2000 | Augustine et al. ........... 607/104 |
| 6,033,432 A | 3/2000 | Augustine et al. |
| 6,071,254 A | 6/2000 | Augustine et al. |
| 6,071,304 A | 6/2000 | Augustine et al. |
| 6,080,189 A | 6/2000 | Augustine et al. |
| 6,083,256 A * | 7/2000 | Der Ovanesian ........... 607/114 |
| 6,094,762 A | 8/2000 | Viard et al. |
| 6,095,992 A | 8/2000 | Augustine |
| 6,102,936 A | 8/2000 | Augustine et al. |
| 6,113,561 A | 9/2000 | Augustine |
| 6,119,474 A | 9/2000 | Augustine et al. |
| 6,123,716 A | 9/2000 | Augustine et al. |
| 6,179,879 B1 | 1/2001 | Robinson et al. |
| 6,183,855 B1 | 2/2001 | Buckley |
| 6,497,720 B1 * | 12/2002 | Augustine et al. ............ 607/96 |
| 6,699,266 B2 * | 3/2004 | Lachenbruch et al. ........ 607/96 |
| 2001/0039391 A1 | 11/2001 | Augustine |
| 2002/0026133 A1 | 2/2002 | Augustine et al. |

FOREIGN PATENT DOCUMENTS

FR 2643814 a * 9/1990 ................. 607/96

* cited by examiner

*Primary Examiner*—Terrell McKinnon
(74) *Attorney, Agent, or Firm*—Harleston Law Firm LLC; Kathleen M. Harleston

(57) ABSTRACT

A support surface for patient comfort, maintaining a cool skin temperature, or reducing the incidence and promoting the healing of bedsores, includes:

(a) a central portion including a hollow, enclosed bladder containing a pre-determined amount of liquid refrigerant with a boiling point between about 23 and about 35 degrees Centigrade;

(b) a flexible spacer mechanism contained in the bladder, the spacer mechanism separating an upper bladder wall from a lower bladder wall; and (c) conductive end portions attached to opposite ends of the bladder, the conductive end portions including a flexible heat conductive material layer.

27 Claims, 18 Drawing Sheets

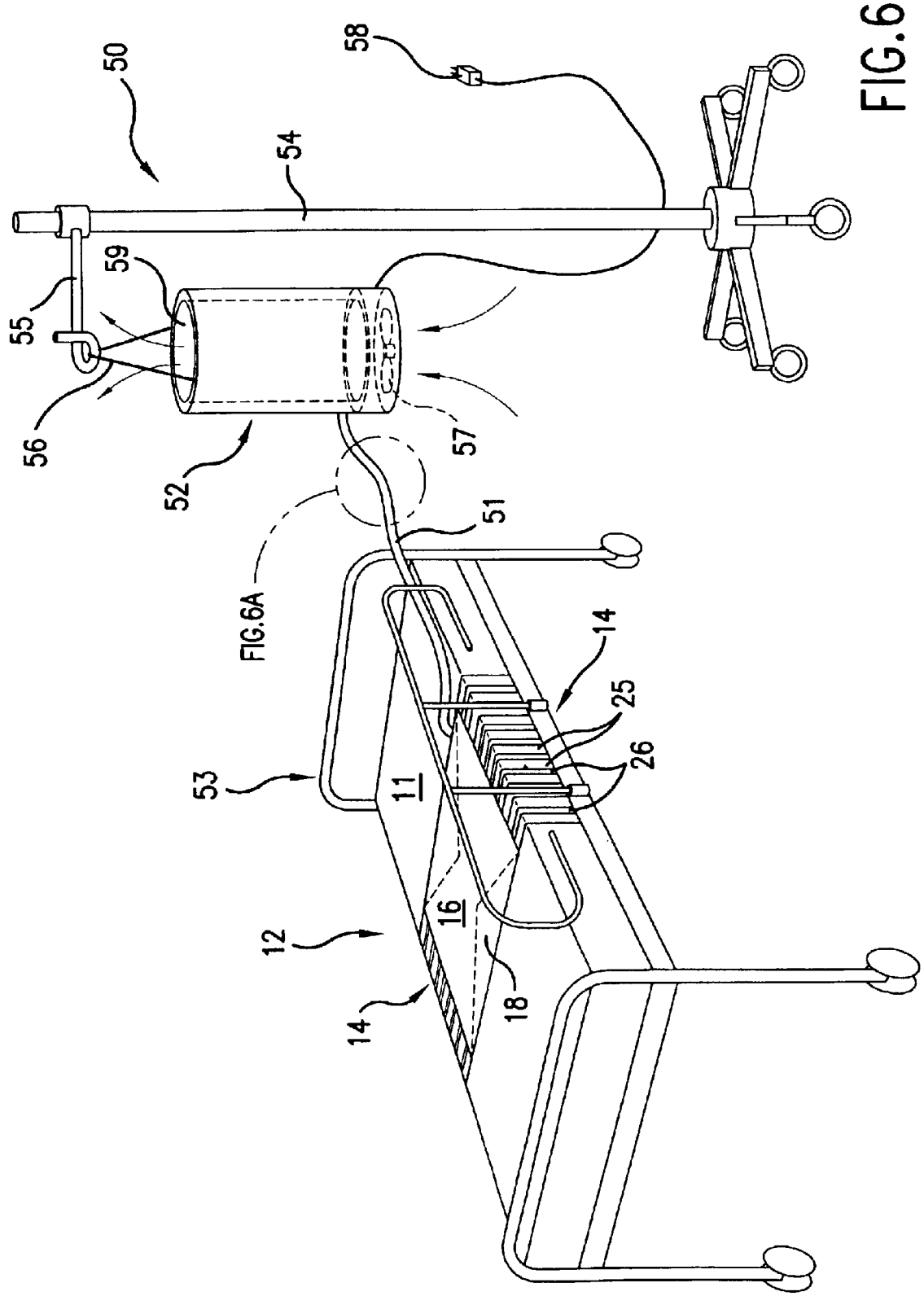

HEAT EXCHANGE SUPPORT SURFACE

BACKGROUND OF THE INVENTION

1. Technical Field

The present device is a cooling support surface with a central, refrigerant-containing bladder bordered by flexible thermal conductive pathways for improving a user's comfort, reducing the likelihood of ulceration, or promoting the healing of bedsores.

2. Background Information

Often, restless sleepers are awakened many times during the night when they become overheated. They uncover themselves, drift off back to sleep, and are reawakened because they are shivering, so they cover up again, and the cycle repeats itself. Another body and temperature-related problem occurs in the cockpit, or in a truck or taxi cab, where high ambient temperatures cause the pilot or driver to sweat and feel faint. He or she is often too busy or trapped behind the wheel and cannot find relief. In addition to physical discomfort, such problems can become severe enough to impair performance and cause accidents. The present cooling support surface provides relief for healthy sufferers, and also for medical patients with more complicated temperature-related or bed bound-related problems.

Bedsores, or decubitus ulcers, can be a serious problem in bedridden or wheelchair-bound patients, particularly for people who are paralyzed, emaciated, post-surgical, elderly, emaciated, or diabetic. Bedsores are a common and persistent problem for those who have to spend a great deal of time in bed, and for their physicians and nurses. As baby boomers age, the elderly population increases, and the ordinary bedsore becomes more of a problem. Bedsores can penetrate to the muscles and bone and are surprisingly life-threatening on occasion. Where, for example, a geriatric patient in a fetal position develops bedsores between his knees, an infected bedsore can become gangrenous and necessitate amputation of a limb. Bedsores can progress to necrosis, septic arthritis, pathologic fracture, and septicemia.

To avoid bedsores, nurses or nurse assistants turn bed-bound patients at prescribed intervals, inspect their skin and apply creams, give massages and baths to patients, exercise limbs, and promptly change wet bed sheets and bedclothes. Patients are placed on air-filled mattresses, sponge rubber "egg crate" mattresses, silicone gel or water mattresses, mattresses filled with fluid or tiny spheres, or Stryker turning mattresses. Protective padding, such as sheepskin or pillows, is placed on bony prominences under braces, casts, etc. Topical ointments, dressings, debridement, and antibiotics are prescribed to curb infections in decubitus ulcers. Prevention and management of bedsores is nevertheless difficult, and further aids are needed.

Bedsores are ordinarily developed over the bony prominences of the body, such as the heels, sacrum (tailbone), ischia, greater trochanters, and ankles (external malleoli). It has been found that bedsores are less likely to form where the skin above the bony prominences is maintained at a slightly cooler temperature than normal skin temperature. The normal core temperature ("normothermia") of the human body is between 36° and 38° C. Skin temperature typically ranges between about 32° C. and about 38° C., depending on ambient temperature, the amount and type of clothing being worn, the core temperature, and where the skin is located on the body. On a typical mattress, seat cushion, seat back, etc., heat is trapped between the body and the covered skin surface and the skin temperature rises rapidly to and is maintained at between about 36 and 38 degrees C. It is believed that skin temperatures in this range promote soft tissue breakdown by increasing tissue metabolism, promoting local perspiration, which wets and weakens the stratum corneum (surface layer of the skin), and increasing friction and shear forces between the sweaty skin and the bedding and/or clothes between the skin and the support surface.

In contrast with a conventional mattress or other resting surface, such as a wheelchair seat cushion or seat, the support surface of the present invention distributes heat away from the user's body during the support period. This keeps the user comfortable while sleeping or sitting, particularly under the user's bony prominences, where bedsores are more likely to form. Relative cooling is accomplished in the present invention with a central, refrigerant-containing bladder connected to thermal conductive pathways that distribute heat from this central bladder to the cooler periphery of the support surface. Cooling is ideally held to a narrow temperature range just below normal skin temperature, since cold temperatures are uncomfortable and undesirable, particularly where the patient is emaciated or otherwise infirm. Thus, in addition to making the user more comfortable and possible preventing accidents and failed missions, the present invention reduces the likelihood of bedsore formation, and aids in the healing of early stage bedsores or other skin ulcers that the user may already have. Since the user's skin is held to a temperature below perspiration threshold (approximately 92 degrees Fahrenheit), the user is relatively free of perspiration and stays more comfortable.

BRIEF SUMMARY OF THE INVENTION

A heat exchange support surface for added comfort, maintaining a cool skin temperature, or reducing the incidence and promoting the healing of bedsores, includes:
   (a) a central portion comprising a hollow, enclosed bladder containing a pre-determined amount of liquid refrigerant, the refrigerant having a boiling point between about 23 and about 35 degrees Centigrade;
   (b) a flexible spacer mechanism contained in the bladder, the spacer mechanism separating an upper bladder wall from a lower bladder wall; and
   (c) thermally conductive end portions attached to opposite ends of the bladder, the conductive end portions comprising a flexible heat conductive material layer.

In an alternate embodiment, a seat/back support surface for comfort and maintaining cool, dry skin, includes:
   (a) a central, hollow, enclosed bladder containing a pre-determined amount of liquid refrigerant, the refrigerant having a boiling point between about 23 and about 35 degrees Centigrade, the bladder being enclosed in a generally horizontal base of the seat;
   (b) a flexible spacer mechanism contained in the bladder, the spacer mechanism separating an upper bladder wall from a lower bladder wall;
   (c) at least one length of flexible tubing attached at both ends into the bladder, the length of tubing extending through a generally vertical back of the seat; and
   (d) a pump in the seat base for pumping a pre-determined amount of the liquid refrigerant up the seat back through a rear section of the length of tubing.

In another alternate embodiment, a seat/back support surface for comfort and maintaining cool, dry skin, includes:
   (a) a hollow, enclosed bladder containing a pre-determined amount of liquid refrigerant, the refrigerant having a boiling point between about 23 and about 35 degrees Centigrade, the bladder being enclosed in a generally horizontal base of the seat;

(b) a main body above the bladder, the main body being comprised of two same-sized, generally rectangular-shaped sheets of a durable, flexible, gas-impermeable material strong enough to contain the refrigerant, the main body sheets being sealed along their edges, except for at least one opening at an upper end and at least one opening at a lower end of the main body, the main body comprising a plurality of channels with staggered openings for allowing the passage of the liquid refrigerant, the main body being on a back of the seat;

(c) at least one length of flexible tubing attached at an upper end to the at least one upper main body opening and at an opposite end to the at least one lower main body opening, the length of tubing extending through the seat back; and (d) a pump in the seat base below the bladder for pumping a pre-determined amount of the liquid refrigerant up the seat back through the length of tubing.

BRIEF DESCRIPTION OF THE SEVERAL VIEWS OF THE DRAWINGS

A more complete understanding of the invention and its advantages will be apparent from the following detailed description taken in conjunction with the accompanying drawings, wherein examples of the invention are shown, and wherein:

FIG. 6 shows a perspective view of an alternate embodiment of a therapeutic support surface and a cooling system according to the present invention, shown in use;

DETAILED DESCRIPTION OF THE INVENTION

Figure 1:
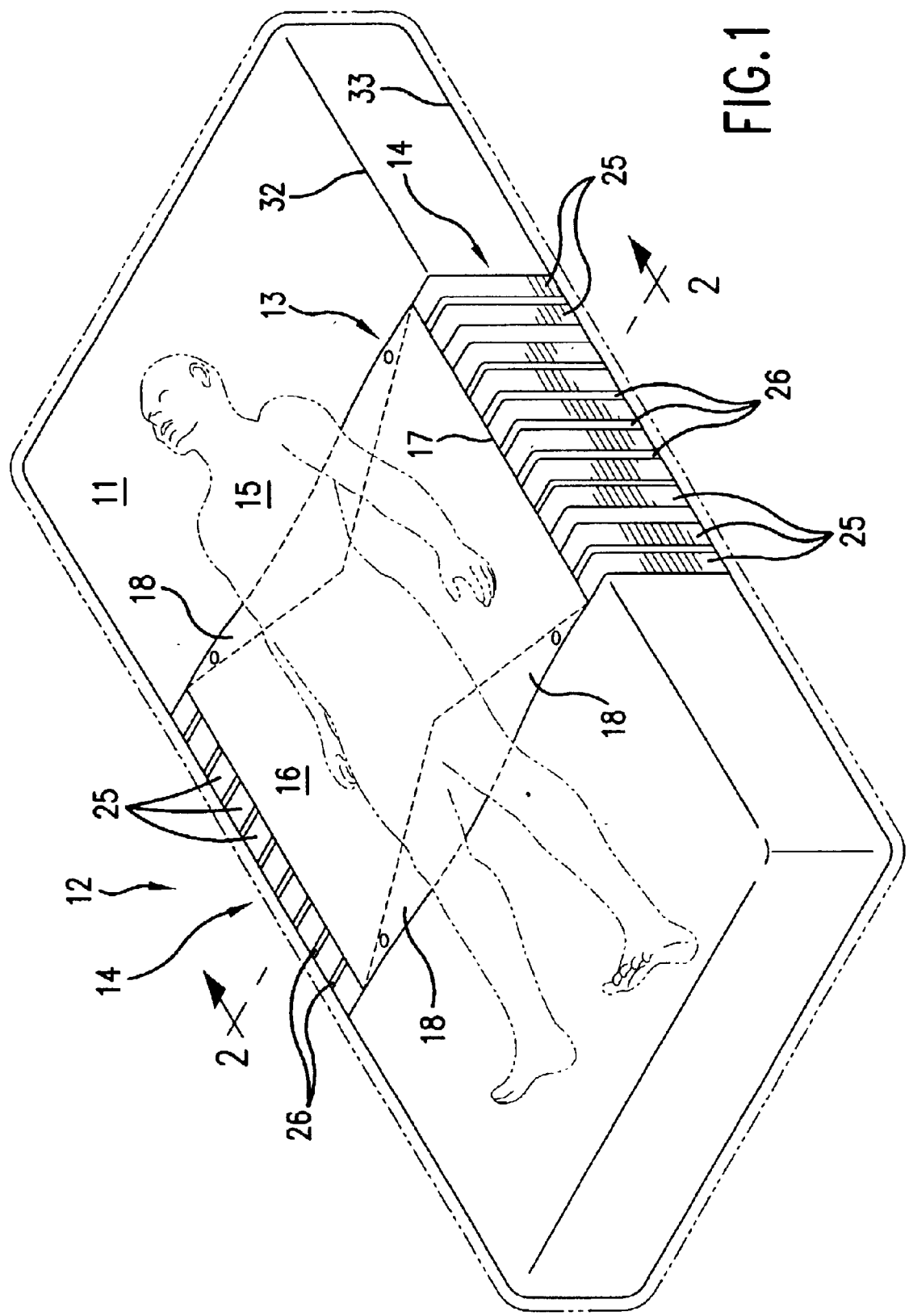
FIG. 1 shows a perspective view of a therapeutic support surface pad according to the present invention, shown in use by a person on a mattress.

In the following description, like reference characters designate like or corresponding parts throughout the several views. Also, in the following description, it is to be understood that such terms as "top," "bottom," "within," and the like are words of convenience and are not to be construed as limiting terms. Referring in more detail to the drawings, the invention will now be described.

Turning first to FIG. 1, a therapeutic support surface, generally referred to as 10, according to the present invention helps to maintain comfort and reduce and promote the healing of bedsores (decubitus ulcers) and the like in persons using the support surface. This therapeutic support surface 10 can be, for example, in the form of a support surface pad 12 placed over a conventional mattress 11, as shown in FIG. 1, or a car seat, seat cushion, child seat, dog bed, or any other type of sleeping, sitting, or resting surface. This support surface 10 can also be in the form of a panel for insertion into a conventional mattress. The present support surfaces 10 can be used in private homes, hospitals, clinics, long term care facilities, hospices, etc. These support surfaces are lightweight, easy to fold and store, and can be cleaned between patients or other users.

Figure 2:
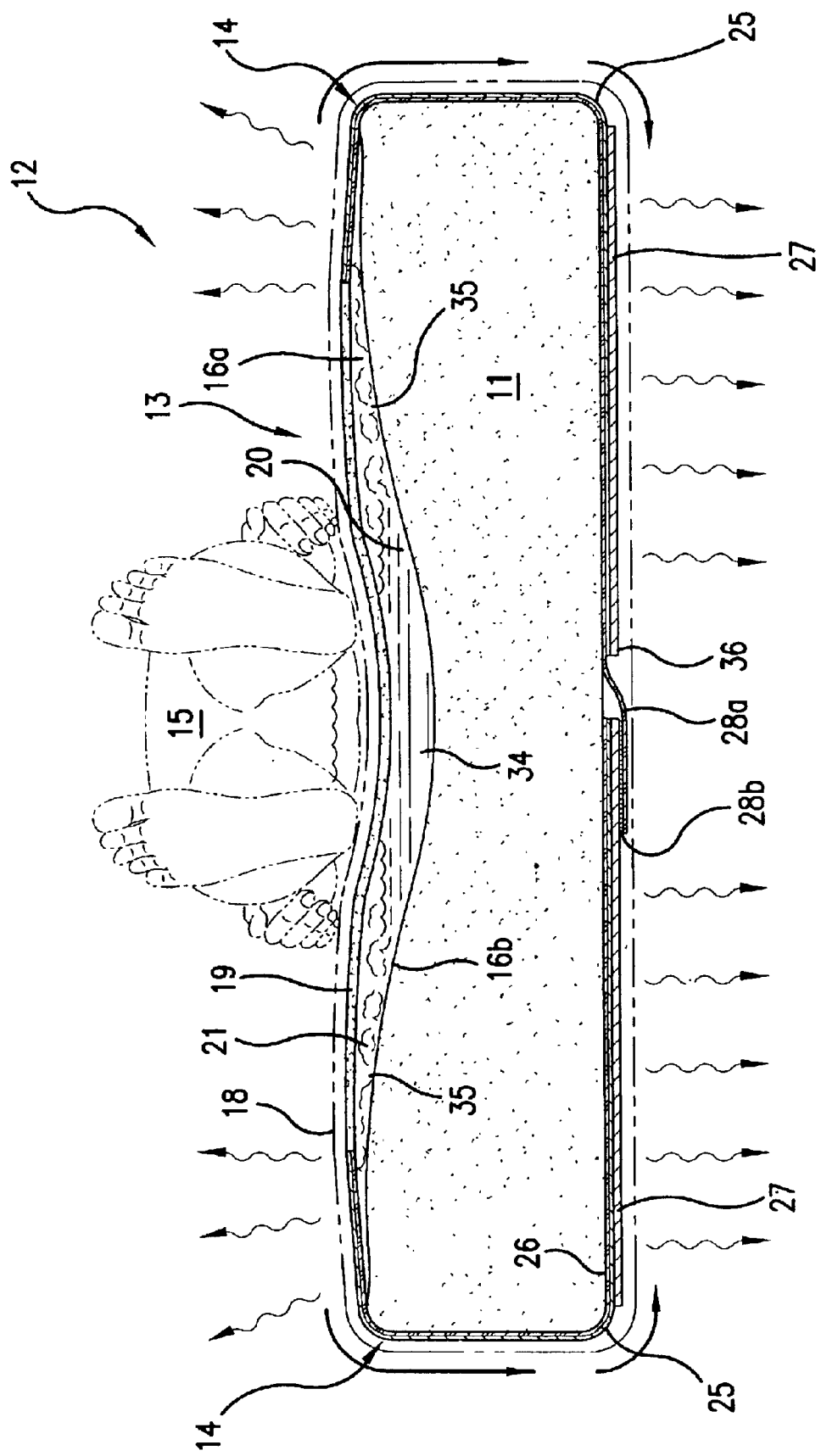
FIG. 2 is a cross-sectional view of the support surface pad of FIG. 1, taken along line 2—2.
Figure 3:
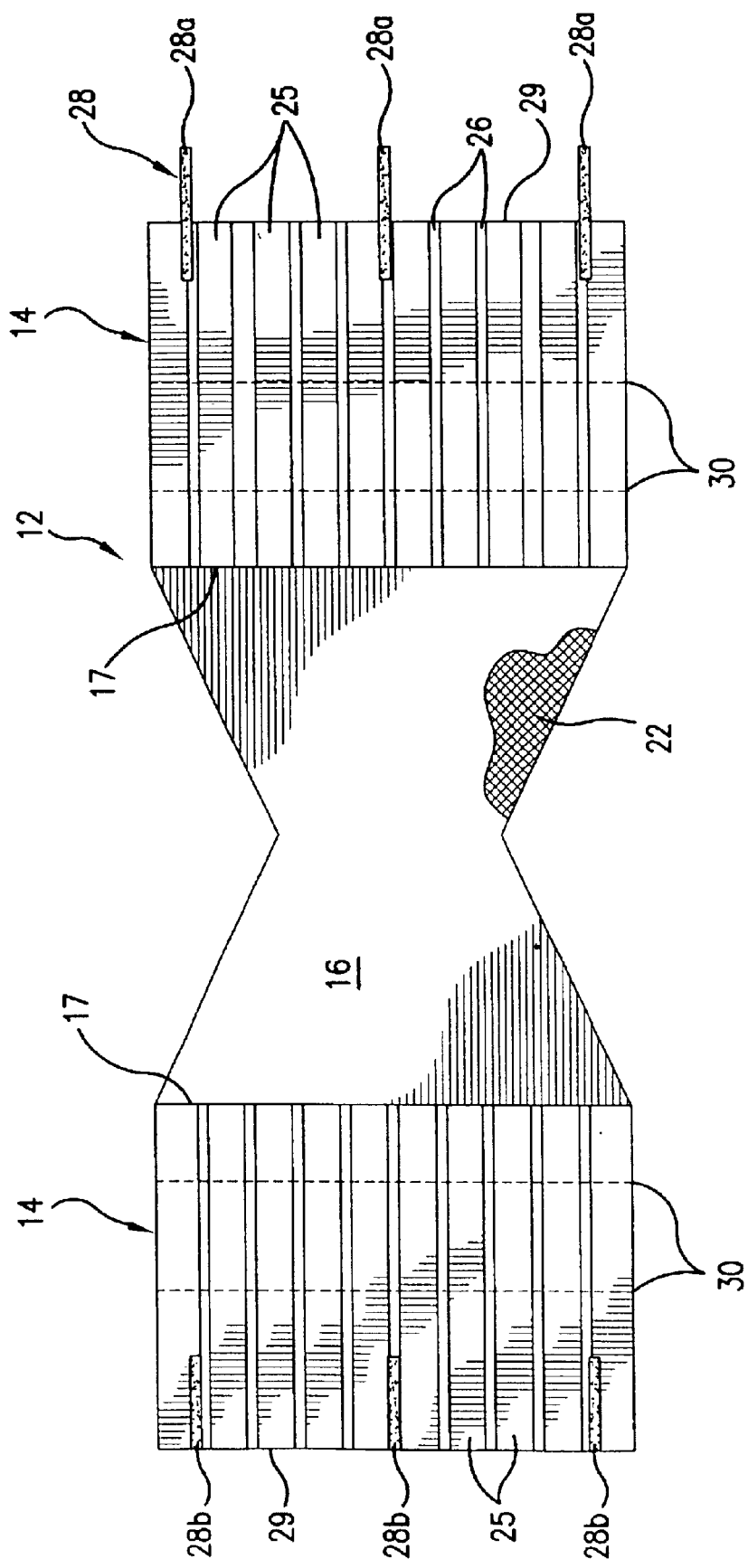
FIG. 3 is a top plan view of a support surface pad according to the present invention.

Referring to FIGS. 1 through 3, a preferred embodiment of a support surface pad 12 is generally rectangular in shape and comprised of a generally bow tie-shaped central portion 13 connected to two opposite, matching, rectangular-shaped conductive end portions 14. As shown in use in FIG. 1, the central portion 13 of the support surface pad 12 is placed on a central portion of a conventional mattress 11, with the conductive end portions 14 of the support pad 12 tucked under the sides of the conventional mattress 11. As shown in FIG. 1, the patient 15 preferably lies on top of the support pad 12, although a second support surface pad can be placed over or under the patient, as desired (not shown). Conventional sheets and blankets can also be used on the mattress, as desired.

As shown in FIGS. 1 and 3, the central portion 12 comprises a generally bow tie shaped heat exchange bladder 16. Opposite end edges 17 of the bladder 16, which are preferably the same length as one another, are connected to two end edges of the conductive end portions 14. The opposite, free end edges 29 of the conductive end portions 14 of the support surface pad 12 are tucked under opposite, long sides of the mattress 11 on which the support surface pad 12 is placed.

The central portion 12 may also include mattress ticking 18, as shown in FIG. 1, which overlays the support surface pad 12. Any suitable ticking 18 material may be used, including nylon or urethane-coated fabric. The ticking 18 provides a cleanable surface which keeps moisture away from the inside of the support surface pad. The central portion 12 preferably also includes a foam, gel, or enclosed silicone fluid upper layer 19 under the ticking. The upper layer 19 lies on top of the bladder 16 for patient comfort.

As indicated in FIG. 2, the substantially leak-proof bladder 16 holds a refrigerant liquid 20, such as hydrofluoroethane. The refrigerant preferably has a boiling point lower than average body temperature and greater than an average room temperature, or between about 23 (73.4 degrees Fahrenheit) and 35 (about 95 degrees F.) degrees Centigrade. More preferred refrigerants 20 include pentafluoropropane, fluorochemical liquid, or a mixture thereof. A most preferred mixture comprises from about 5 to 50 weight % of 1,1,1,3,3-pentafluoropropane, and from about 50 to 95 weight % of a fluorochemical liquid. The most preferred mixture has a boiling point between about 80 and 90 degrees Fahrenheit. The refrigerant 20 condenses at a lower temperature than average body temperature.

Sufficient space is left in the bladder 16 for expansion of the refrigerant liquid 20. When the user lies on the bed, the portion of the bladder 16 under the body is depressed by the weight, as shown in FIG. 2. The refrigerant liquid 20 tends to flow to and puddle in that lower area within the bladder 16. If heat from the body is above the boiling point of the refrigerant 20 within the bladder, heat from the body lying anywhere on the upper surface of the bladder 16 causes the refrigerant 20 to boil and vaporize. Vapor 21 (gas) is indicated in FIG. 2. Importantly, the bow tie, or butterfly, shape has been found herein to allow a high ratio of area in which heat is being exhausted to the environment over the area in which heat is being withdrawn from the body. This is also true of shapes similar to a bow tie, such as a butterfly or bat wing shape, or a general "H" shape, with longer, matching sides and a narrower center bridging the sides. These similar shapes also convey this benefit and are included herein.

The bladder 16 is made of a durable, flexible, gas-impermeable material, so that it is comfortable to sit or lie on, and is strong enough to contain the refrigerant 20 and withstand liquid to gas cycling over time. The bladder 16 is enclosed, so that the refrigerant does not escape. Even if the amount of refrigerant 20 is found to decrease slightly over time in the bladder 16, the bladder can be periodically serviced and recharged. The bladder is preferably coated, more preferably by spraying or painting on a coating, with a visco-elastic urethane material. The visco-elastic urethane produces more favorable mechanical characteristics, and deadens any crinkling sounds, which may occur when the patient moves on the support surface pad 12.

In the interior of the hollow bladder 16 substantially parallel to upper and lower surfaces 16a, 16b, respectively, of the bladder is a compliant spacer mechanism 22, preferably a three-dimensional floating net, as shown in the cutaway portion in FIG. 3. Movement of the refrigerant liquid 20 is preferably not restricted within the bladder 16. A preferred net 22 has small, four-sided openings between thin strands of a flexible, refrigerant-resistant material. As the user moves on the support surface pad 12, the refrigerant liquid flows within the bladder, back and forth through the openings and along the strands in the net. The net 22 is substantially free-floating, and preferably extends the full length and width of the bladder 16. One or more side edges of the net 22 may be joined, as by heat sealing (preferred), sewing, or welding, into the seam between the upper and lower surfaces of the bladder. The bladder may alternatively be a single piece of folded-over bladder material. The net 22 helps to keep the upper and lower walls of the bladder 16 at least a short distance apart despite compression from the body or other weight on the support surface 10. In addition to helping maintain integrity, the net 22 helps to distribute the refrigerant 20 within the bladder 16.

Figure 4:
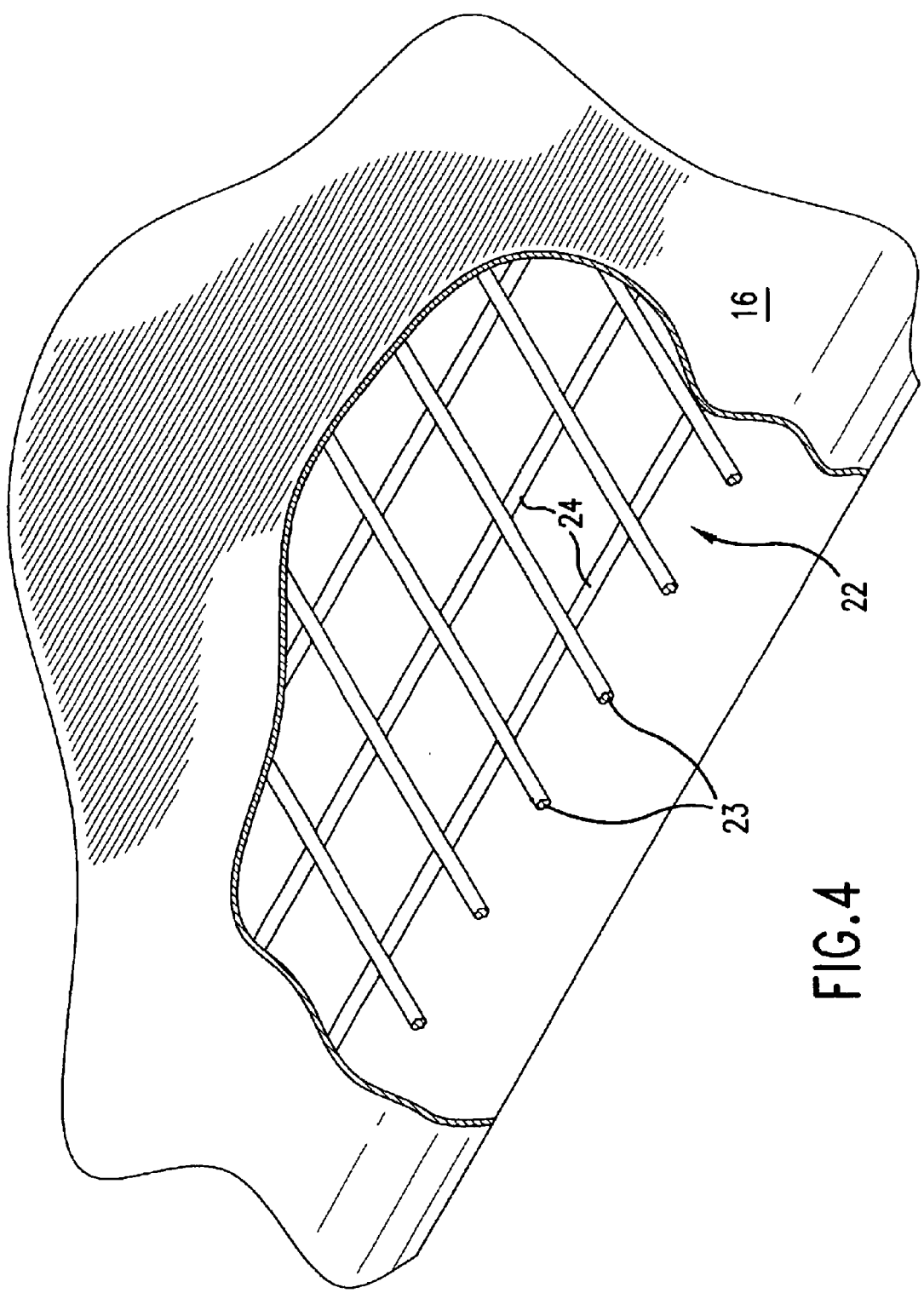
FIG. 4 is a cutaway perspective view of a portion of a bladder of a support surface according to the present invention.

As shown in FIG. 4, a specialized capillary net 22 is preferred. The capillary net is composed of two or more layers of strands that lie on top of one another, so that the strands do not impinge on one another. The strands act as capillary flow pathways for drops of refrigerant. The size of the spacing between the net strands is dictated in part by the surface tension and viscosity of the refrigerant being used in the bladder. Parallel strands 23 of this fine net 22 lie on top of, and are affixed to, the cross-strands 24 of the same net, as shown in FIG. 4. The cross-strands 24 are parallel to one another and overlay the strands 23 on top of them. This configuration promotes capillary action, where refrigerant vapor particles caught on a strand travel down along that strand 23 without being broken by a cross-strand 24. The same is true of the reverse (bottom) face of the net: refrigerant vapor particles caught on a cross-strand 24 can travel down along that strand unimpeded. In addition to providing a thin backbone for the bladder 16, and acting as a physical barrier between the upper and lower walls 16a, 16b of the bladder, the net 22 allows flow space and acts as a flow-through, inert substrate for the refrigerant. The net 22 helps the support surface 10 to be effective even though the support surface is being compressed by the user's body weight.

Figure 3A:
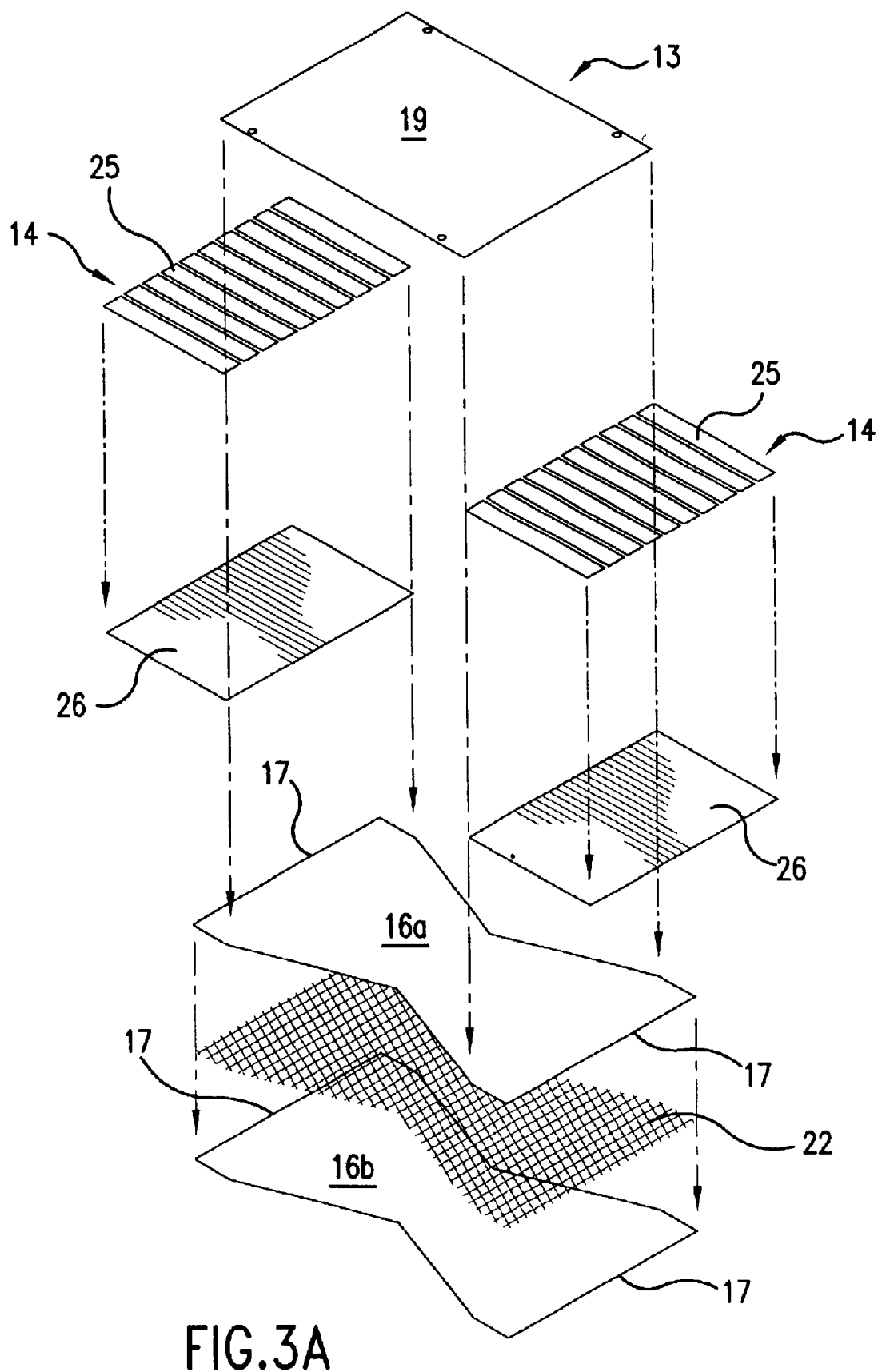
FIG. 3A is an expanded view of layers of a section of a support surface pad according to the present invention.

As shown in FIGS. 1, 3 and 3A, the conductive end portions 14 of the support surface pad 12 include thermally conductive pathways 25 for conducting heat away from the central bladder 16 and dissipating it. The conductive pathways are made of a thin, flexible, thermally conductive material. The conductive material has a conductivity greater than about 80 watts/meter—degree Kelvin. Metals such as copper or aluminum are preferred. The conductive pathways are preferably between about 0.001 and 0.050 inch in thickness. Very thin (about 0.005 to 0.010 inch thick) sheets of copper, or a combination of copper and aluminum, are more preferred because they are effective, yet comfortable to lie or rest on.

In an alternate embodiment, the conductive pathways 25 are thicker where they connect to the bladder, thinning where they bend around the sides of the mattress and go under the mattress 11. Although in some embodiments, thicker conductive pathways 25 do not wrap under the mattress, they are preferably long enough to wrap around under the mattress 11, as shown in the preferred embodiment of FIGS. 2 and 3. A pathway length of about 6 to 12 inches is most preferred. The conductive pathways may alternatively extend away from the mattress itself to exhaust heat directly into the ambient air.

An alternate embodiment is comprised of laminated thin sheets (each layer being several thousandths of an inch in thickness) of conductive pathway material. Also, the thin sheets 25 may alternate materials, such as alternating copper and aluminum layers adhered to one another.

Since many hospital/nursing home beds have a top or bottom portion that can be raised and lowered, a solid metal sheet may not be comfortable or practical. Therefore a preferred embodiment herein includes a support surface pad 12 with conductive pathways 25 made of thin, same-size, rectangular strips of copper, aluminum, silver, thermally conductive polymer, combinations thereof, or any other highly thermally conductive material, as shown in FIGS. 1, 3 and 3A. Suitable conductive materials include tape, foil, plate, or flashing composed of aluminum, copper, silver or other highly conductive material; copper or aluminum cable, or braided or solid sheet metal. The conductive strips 25 are welded or otherwise attached together side by side, as shown in FIG. 3A, or alternatively are attached by their bottom surface (as by gluing) to a flexible, non-conductive material 26, such as a polyurethane mattress ticking, which is visible between each conductive strip, as shown in FIG. 1, for added flexibility and comfort. The conductive strips 25 conduct the heat, and the flexible, non-conductive material 26 under/between the conductive strips allows the sides of the mattress 11 on which the support surface pad 12 is placed to flex when the head or foot portion of the bed is raised or lowered. It has been found herein that these preferred thin copper strip pathways 25 are advantageous in that they are superior heat conductors, yet are comfortable to rest on and allow movement of the bed or other surface on or in which the support surface rests.

One end of each conductive strip 25 overlaps the lower bladder wall 16b at an end 17 of the bladder. The upper faces of these end portions of the conductive strips 25 are preferably affixed to the outside of the lower bladder wall 16b using an adhesive that bonds to metal, or by spot welding. It has been found that a heat conductive adhesive enhances transfer of heat from the bladder 16 to the conductive strips 25. The lower faces of the remainder of the conductive strips 25 are attached, as by gluing, to the flexible, non-conductive material 26. Conductive strips may also be glued to the top edges of the bladder to withdraw maximum heat from the edges in order to keep the bladder as cool as possible.

FIG. 3A shows the separate layers of the support surface pad 12. The central portion 13 includes a generally rectangular-shaped foam, gel, or enclosed silicone fluid upper layer 19, which is superimposed on the generally bow tie-shaped, hollow bladder 16. As indicated by the arrows in FIG. 3A, the upper bladder wall 16a is attached along its edges to the lower bladder wall 16b, with the generally bow tie-shaped net 22 in between the two bladder walls 16a, 16b. Each bladder end 17 is attached to a conductive end portion 14. Each conductive end portion 14 includes an upper layer with conductive pathways 25. The conductive pathway layer shown includes side by side, same-size copper strips. The lower surfaces of the side-by-side strips are attached to one (preferred) or two flexible, durable, non-conductive superimposed layers 26. The flexible non-conductive layer 26 is preferably the same length and width as the conductive end portion 14. In addition to providing cushioning, the foam, gel, or enclosed silicone fluid layer 19 has been found to muffle crinkling sounds that the preferred copper strip pathways 25 sometimes emit as the user moves around on the support surface.

In the preferred embodiment shown in FIGS. 2 and 3, a number of lock and loop strips 28 are attached at one end to a free end 29 of each conductive end portion 14. As shown in FIG. 3, the ends of the lock and loop strips 28, which are oriented in the same direction as the conductive pathways, overlap the free end 29 of the conductive end portion 14. On one conductive end portion 14, the lock and loop strips 28b do not extend beyond the end 29 of the conductive end portion. On an opposite conductive end portion 14, the lock and loop strips 28a extend beyond the end 29 of the end portion, so as to overlap the corresponding lock and loop strips 28b on the end of the opposite conductive end portion 14 when the support surface pad 12 is in place on a mattress 11, as shown in FIG. 2. Three sets of lock and loop strips 28 are shown in FIG. 3. The broken lines in FIG. 3 indicate fold marks 30, where the conductive end portions 14 bend around the upper 32 and lower 33 side edges of the mattress 11, as shown in FIG. 1.

Continuing with FIG. 2, the support surface pad 12 optionally includes matching thin conduction plates 27, each attached to an end of a conductive end portion 14. A large conduction plate or series of conduction plates 27 fit between the mattress 11 and a box spring or bed. They further conduct heat from the conductive pathways 25 wrapped around the sides of the mattress 11. Their purpose is to sink heat and aid in transferring heat downward to the bed frame. Like the conductive pathways 25, conduction plates 27 can be made of copper, aluminum, silver, thermally conductive polymer, combinations thereof, or any other highly thermally conductive material. The conductive strips may be substantially thicker closer to the bladder edge, with their thickness tapering off further away from the bladder. Also, the support surface may include a foam or gel comfort pad on top of the bladder and under the ticking. Heat is conducted through the comfort pad to warm the bladder.

When a person sits or lies on a support surface, his or her body heat begins to warm the support surface. The refrigerant liquid 20 in the bladder 16 under the body is quickly heated by body heat to its boiling point. This area under the body is called here the "warm zone" 34. The weight of the body on the soft mattress ensures depression of the reservoir of refrigerant 20 in the bladder relative to the edges of the support surface pad. The refrigerant liquid 20 then converts to a gas or vapor 21, inside the bladder 16, which is shown in FIG. 2. The vapor 21 expands toward "cool zones" 35. The "cool zones" 35 here are the areas of the support surface 10 that are not heated by the body, generally the right and left side areas of the support surface pad. As the vapor 21 expands toward the cool zone 35, it condenses and rejects heat at the periphery of the bladder.

The refrigerant liquid 20 then flows back to the warm zone 34 for a second cycle of heating and cooling. This has the effect of keeping the area under the body cool. The body parts, such as the loaded bony prominences, that sink more deeply into the central sink have greater surface area in contact with the support surface pad 12 and therefore are more exposed to the cooler temperature. The lack of body weight causes the cool zones to be elevated above the weighted warm zone. Gravity encourages the flow of the condensed refrigerant liquid 20 back to the warmest, lowest region, which is frequently along the centerline of the mattress/pad, where people often choose to lie. Support surface pads 12 can be made for smaller, single bed mattresses, and for double, queen, and king size beds. In the latter case, the bladder will also easily accommodate several bodies lying side by side.

A further cooling effect is provided by the conductive end portions 14. Heat at the periphery of the bladder 16 is transferred to the conductive pathways 25, which heat up starting at the ends of the conductive strips 25 that are nearest to the ends 17 of the bladder 16. The advantage of overlapping the ends of the conductive pathways over the edges of the bladder is enhanced absorption of heat from the bladder. Although the conductive pathways 25 very gradually heat up to their free ends 36 under the mattress 11, as indicated by the descending arrows in FIG. 2, the heat dissipates off into the surroundings, as indicated by the wavy arrows in FIG. 2. Surprisingly, even though the support surface 10 is under compression (by the user's body), it works to keep the patient or other user cool and comfortable while sleeping or resting on the support surface 10.

Use of the support surface pads 12 can be customized for different patient/user needs. For example, a heart patient with edematous lower legs can place the support pad under her lower legs before she goes to sleep at night; a person with tennis elbow can sleep with a support surface pad under her midsection; or a user whose lower back tends to sweat might use a support surface on his chair during work hours, or it could be used in conjunction with a car seat. In general, warmer areas of the body, such as the sacrum, trunk, and generally proximal regions, may require more cooling than cooler, distal regions of the body, such as the ankles and heels, which may require little or no cooling. Support surfaces 10 herein may be any size and may be custom designed to suit tall or short people, small or large sized people, etc.

Figure 5:
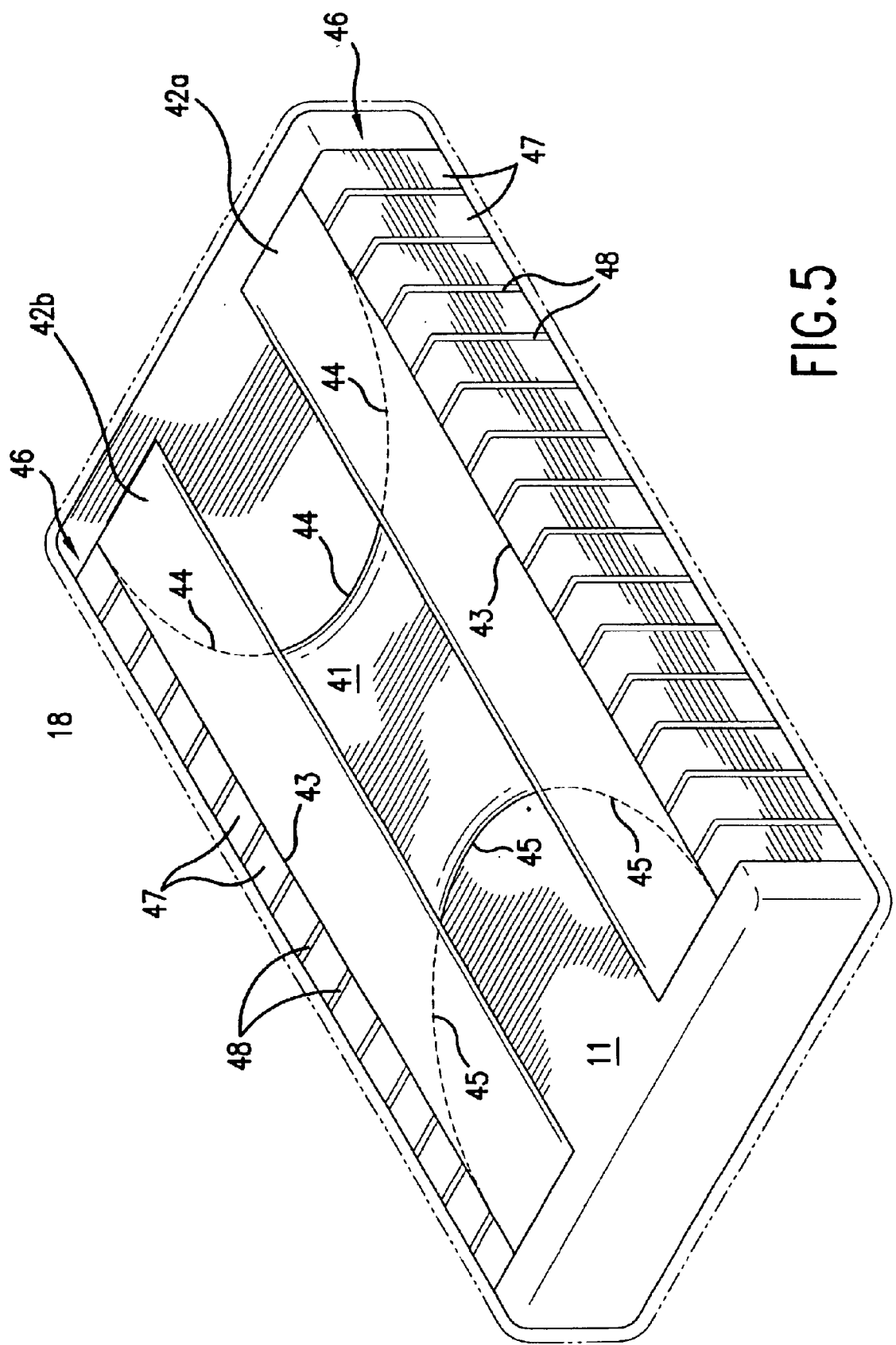
FIG. 5 shows a perspective view of an alternate embodiment of a support surface according to the present invention, shown on a mattress.

Turning to the alternate embodiment shown in FIG. 5, a generally H-shaped dual bladder support surface system 40 includes a first, central, generally H-shaped bladder 41 between two matching second, bar-shaped bladders 42a, 42b. Each second bladder 42 substantially overlaps an end section 43 of the first bladder 41. The second bladders 42, which are equal in length, are elevated slightly above the plane of the first bladder 41. The end sections 43 of the first bladder 41 are delineated by the curved dashed lines, and ends 43, in FIG. 5. The top 44 and bottom 45 edges of the first bladder are curved, while the ends 43 are straight. The far ends 43 of all three bladders 41, 42 are aligned along line 43 in FIG. 5. The bladders 41, 42 are enclosed and are not interconnected. All three bladders preferably contain a floating net 22 lying parallel to the upper and lower surfaces of the bladders.

The dimension from one end 43 of the first bladder 41 to the other end 43 may vary, although it is restricted by the width of standard mattresses/beds (single, double, queen, king). The dimension of the narrowest point of the bridge between the upper 44 and lower 45 edges of the first bladder may vary, although performance of the support surface is optimized when this dimension is between ⅙ and ⅔ of the length of the ends 43 of the first bladder. This is also true of the alternate embodiments described herein. The upper and lower edges 44, 45 of the first bladder 41 may be angled, as shown in FIG. 1, or curved, as shown in FIG. 5. In some embodiments, the bladder 16 does not have parallel walls, and has a pronounced flare as it extends away from the user's body to the cool zones at the edges. This flared region may extend the entire length of the bed at the edges.

The first, warmer bladder 41, which absorbs body heat from the user lying on its central section, contains a refrigerant liquid with a boiling point between about 83 and 90 degrees Fahrenheit. The second, cooler bladders 42 absorb heat from the first bladder 41 and therefore contain a different refrigerant liquid with a boiling point that is lower than the boiling point of the refrigerant in the first bladder, preferably between about 75 and 83 degrees Fahrenheit. The refrigerant in both bladders 41, 42 is preferably a blend of a pentafluoropropane, most preferably 1,1,1,3,3-pentafluoropropane, and a fluorochecmical liquid. The relative proportions of the two components varies according to the desired boiling point of the refrigerant.

Continuing with FIG. 5, both of the second bladders 42 are connected along one end 43 to conductive end portions 46. The conductive end portions 46 comprise conductive pathways 47, which are preferably copper and/or aluminum strips. The bottom faces of the conductive pathway strips are attached to a base layer of flexible, non-conductive material 48 so that they are parallel to one another. Once the dual bladder support surface 40 is placed on a mattress 11, these opposite conductive end portions 46 fold around the sides of the conventional mattress 11 and under the mattress, as shown in FIG. 5. The dual bladder support system 40 is enclosed in mattress ticking 18, which is cleanable.

Alternatively, the first bladder 41 may be connected to conductive end portions 14 on its opposite ends in addition to, or instead of the second bladder conductive end portions 46. Alternatively, the support surface may not have any conductive end portions; instead, it may have only first and second bladders.

As in the first, single bladder embodiment 12, refrigerant in the first bladder 41 of this second, dual bladder embodiment 40 pools in the warm zone under the user's body when the device is in use. The user's body ordinarily lies between the second bladders 42 on a central part of the first bladder 41. As the refrigerant reaches its boiling point, it vaporizes within the first bladder. The vapor rises to the cooler end sections of the first bladder 41. Heat from the first bladder is transferred to the second bladders 42 on both sides of, and just above, the first bladder. As the refrigerant in the second bladders 42 reaches its boiling point, it vaporizes within the second bladders. The vapor rises to the cooler end sections of the second bladders 42. Heat is transferred from there to the conductive pathways 47 on the far end of each second bladder 42. As the pathways 47 conduct heat, the heat dissipates to the surroundings. The overall effect is to keep the user cool over time. This self-contained embodiment provides enhanced cooling capacity, which is useful for situations such as a patient with a large body or a fever, or where ambient (e.g., room) temperature is warm.

Figure 6A:
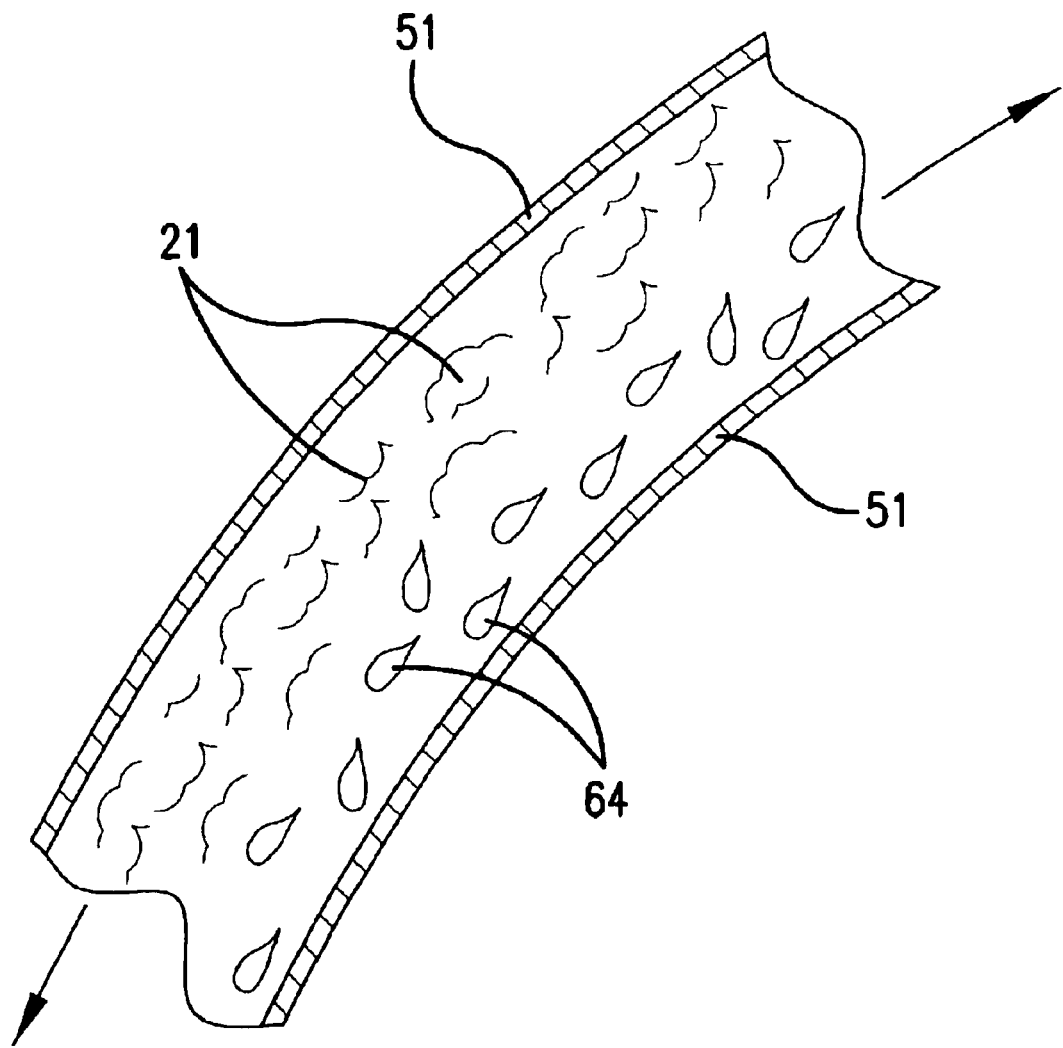
FIG. 6A is a cross-sectional view of a portion of a cooling tubing of the cooling system of FIG. 6.
Figure 6B:
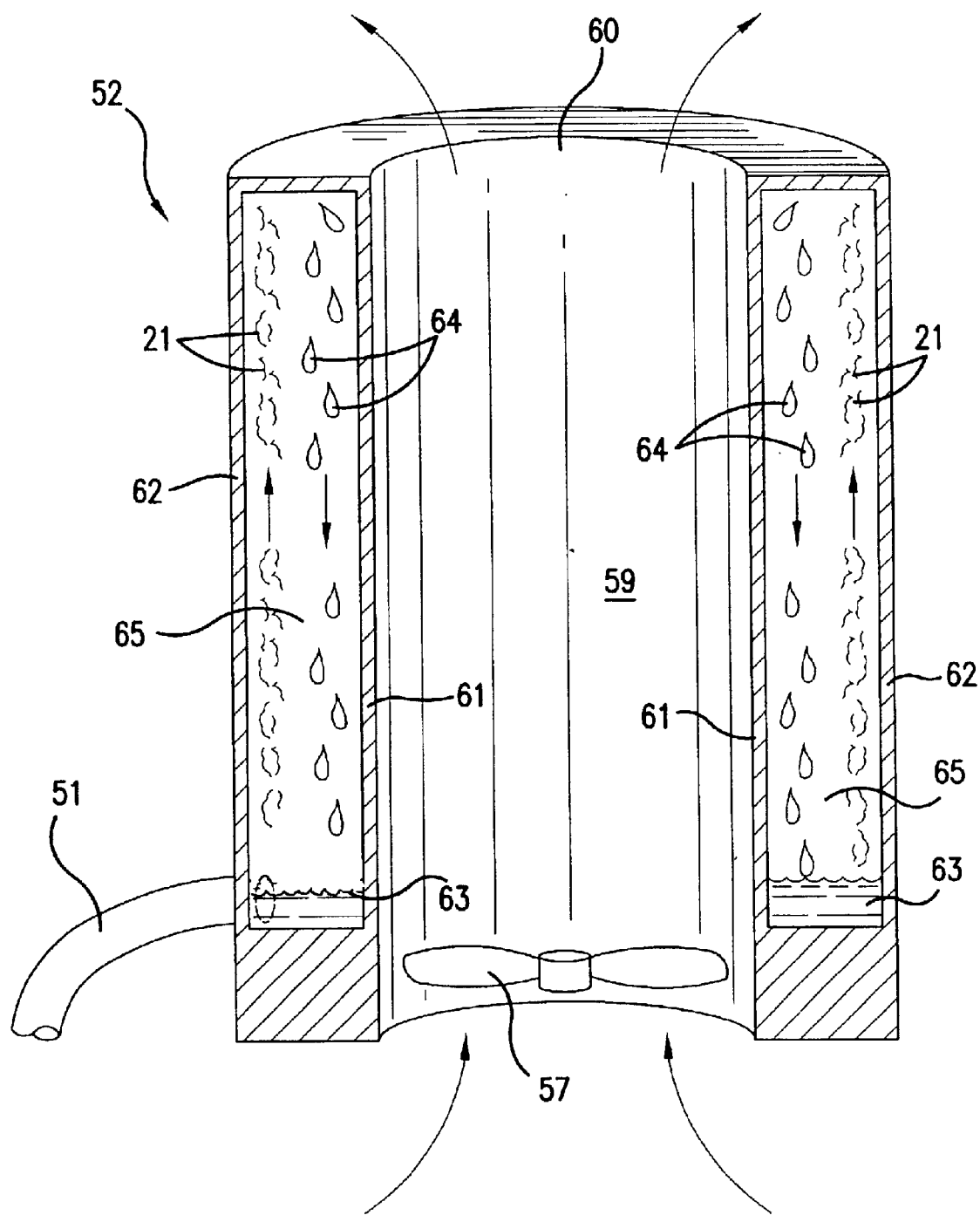
FIG. 6B is a cutaway perspective view of a portion of the cooling system of FIG. 6.

Referring to FIGS. 6, 6A and 6B, an alternate embodiment of the present invention includes an external cooling system 50 attached by tubing 51 to a bow tie-shaped bladder 16 of a support surface pad 12. The opposite ends of the bladder 16 are attached to conductive end portions 14, which are tucked under the mattress 11 of a hospital bed 53. The conductive end portions include conductive pathways 26, the bottoms of which are attached to a flexible, non-conductive layer 26.

As shown in FIG. 6A, one end of the cooling system tubing 51 is attachable to a sealable fitting (not shown) allowing access to the interior of the bladder 16. An opposite end of the cooling system tubing 51 is attached to a high surface area heat dissipation device, preferably a lantern-shaped cooling device 52, which is held up above the level of the bed 53 by any suitable means, preferably a conventional IV (intravenous bag) stand 54. An arm 55 of the IV stand 54 holds a flexible handle 56 of the cooling device 52. If desired, the bladder fitting can be capped and the support surface pad 12 can be used on its own, as described herein.

As shown in FIGS. 6 and 6B, a low-powered electric fan 57 in the bottom of the cooling device receives electricity via an electrical plug/wire 58. When it is on, the fan 57 urges ambient air upward, as indicated by the arrows, through the bottom of the cooling device, through a hollow center 59 of the lantern-shaped cooling device 52, and out the open upper end 60 of the top of the lantern-shaped cooling device. Parallel interior 61 and exterior 62 side walls of the cooling lantern 52 define a circular, closed space 65 that holds a liquid refrigerant 63. The fluid then trickles down from the cooling device to the bladder in the bed for another cycle. As the refrigerant heated to its boiling point, vapor 21 is formed. As the vapor 21 is cooled by the fanned air passing through the hollow center 59 of the cooling device, it evaporates, forming droplets 64 of refrigerant. The hollow center 59 provides an additional area of convective flow. The droplets trickle down to the bottom of the space 65.

As indicated by the arrows in FIG. 6A, hot vapor 21 passes through the cooling tube 51 into the base of the space 65 in the cooling lantern 52. The cooling tube 51 is preferably at approximately a 30 to 45 degree angle relative to the pad 12. The refrigerant vapor 21 passes through the tubing 51 between the cooling system and the bladder 16 in both directions. Some of the vapor 21 evaporates along the tubing 51, forming droplets 64 of refrigerant, as shown in FIG. 6A. This embodiment provides enhanced cooling capacity for long-term use or situations with a high heat load. Heat is transferred to the cooling lantern, which is remote from the patient, where the heat is dissipated.

Figure 7:
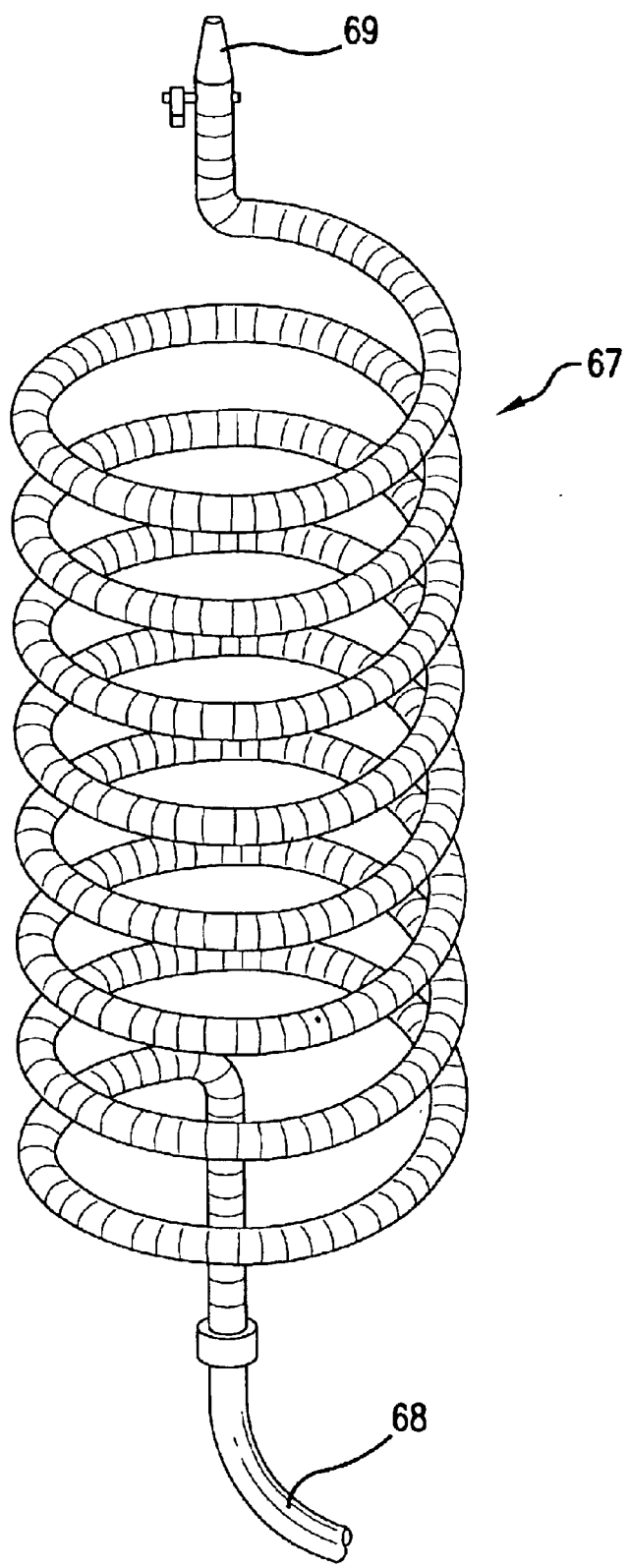
FIG. 7 is a perspective view of a coiled cooling tube according to the present invention.

Turning to FIG. 7, in an alternate embodiment, the external cooling system comprises a coiled cooling tube 67 rather than a cooling lantern. One end 68 of the coiled cooling tube 67 is removably attachable to a fitting leading to the interior of a bladder 16, as shown in FIG. 6. The cooling tube 67 may coil, for example, up a bedpost or a movable pole alongside the bed the bladder is on. Refrigerant vapor moves up the coiled cooling tube. The coiled cooling tube may be cooled by a conventional fan blowing on the exterior of the cooling tube. As the vapor cools, it forms droplets, which trickle down the interior walls of the coiled cooling tube (by gravity), and back into the bladder. The opposite end of the coiled cooling tube 67 is connected to a pressure relief valve 69 for periodically releasing pressure inside the coiled cooling tube.

Figure 8:
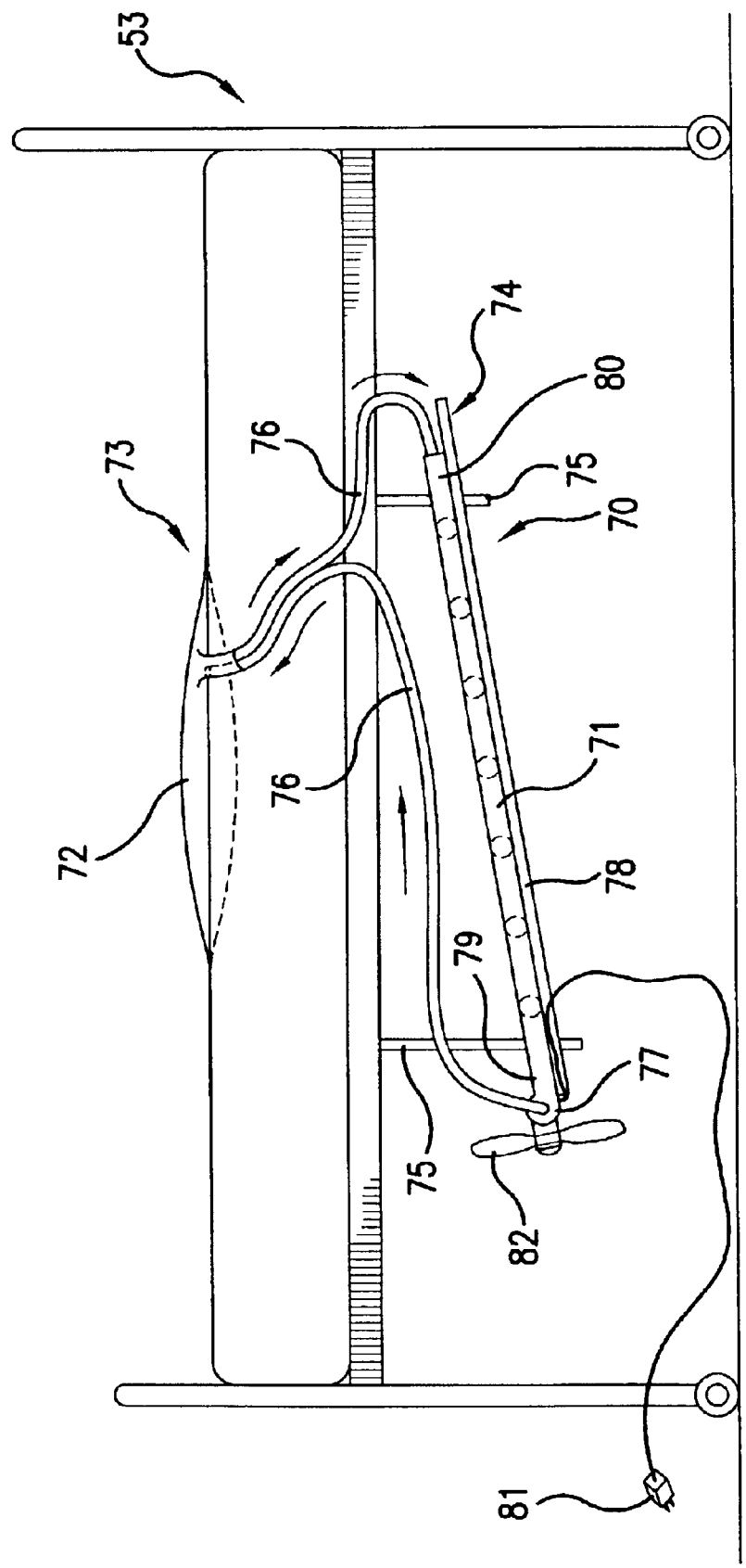
FIG. 8 is an elevational side view of an alternate embodiment of a support surface and a cooling system according to the present invention, shown in use.

Turning to FIG. 8, a third embodiment of an external cooling system 70 comprises a cooling cylinder 71, operable pump 77, and tubing 76, and preferably a cylinder support 74. The cooling cylinder 71 is connected by tubing 76, preferably two one-way tubes, to a bladder 72 of a support surface. Here, the support surface is a mattress 73. As shown in FIG. 8, the bladder 72 is mounted at the top center of the mattress 73. The external cooling system 70 fits under or next to a hospital bed 53 on which the support surface mattress 73 has been placed. In the embodiment shown in FIG. 8, the cylinder support 74 is mounted under the hospital bed 53 by support arms 75 and supports the cooling cylinder 71. The cooling cylinder 71 is mounted on a platform 78 of the cylinder support 74, with the lower, posterior end 79 of the cylinder being below the level of its higher, anterior end 80. The cooling cylinder is preferably at about a 30 to 45 degree angle with respect to the horizontal axis of the mattress. A small electrical pump 77 operated by means of an electrical plug/wire 81 is mounted at the lower end 79 of the cooling cylinder. The pump 77 is operable to pump refrigerant through the tubing 76 back up to the bladder. The cooling cylinder 71 may be cooled by an attached fan 82 blowing on the outside of the cylinder from the lower end of the cylinder.

In use, refrigerant liquid and/or gas from the central bladder 72 travels down a first tubing 76a by gravity. A higher end of the first tubing 76a is closely fitted to an opening in the bladder. An opposite, lower end of the first tubing 76a is inserted into the higher end 80 of the cooling cylinder 71 just prior to use of the external cooling system. As the gas passes down through the cylinder, it cools and condenses into liquid, which flows by gravity down to the lower end 79 of the cooling cylinder. When it cools, refrigerant at the lower end of the cooling cylinder 71 is pumped back up a second tubing 76b through the same fitting on the bladder 72.

Figure 9:
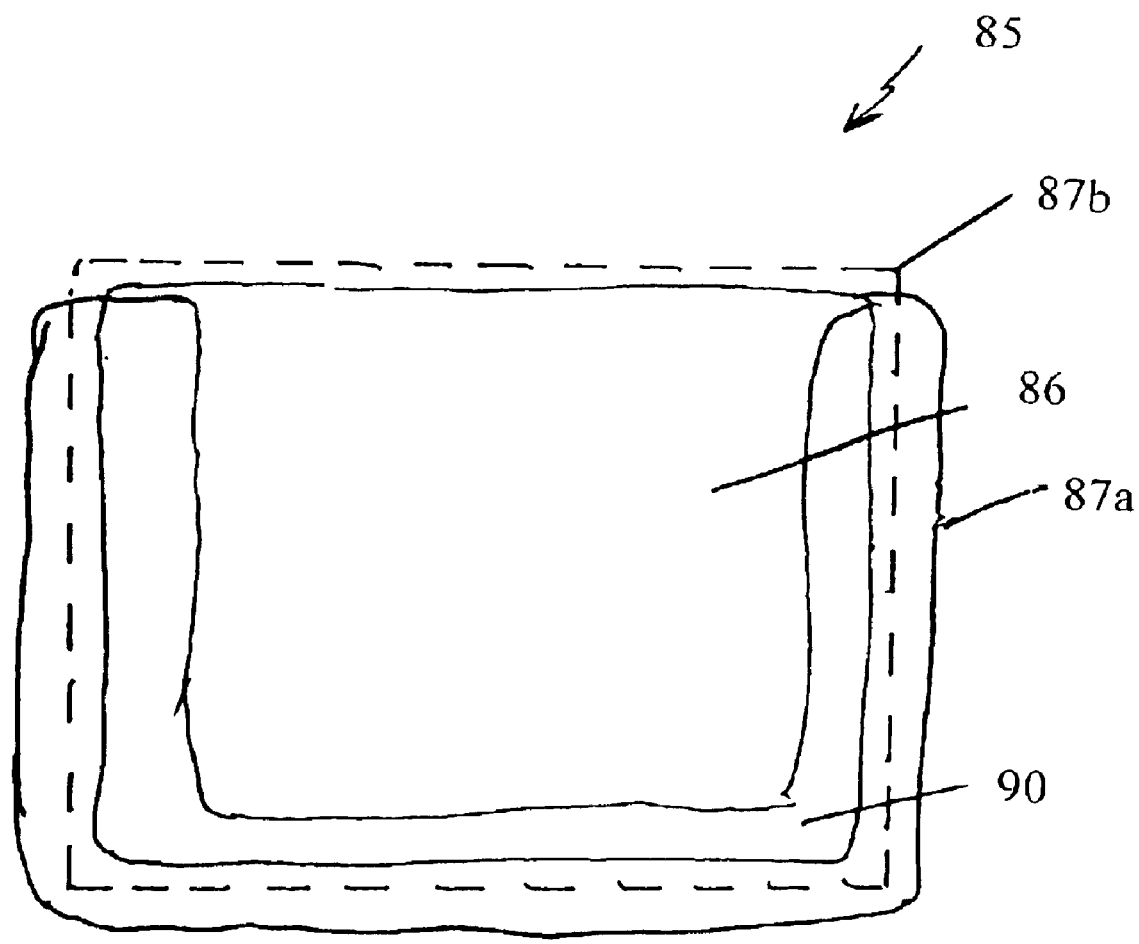
FIG. 9 is a top plan view of an alternate embodiment of a seat cushion support surface according to the present invention.
Figure 10:
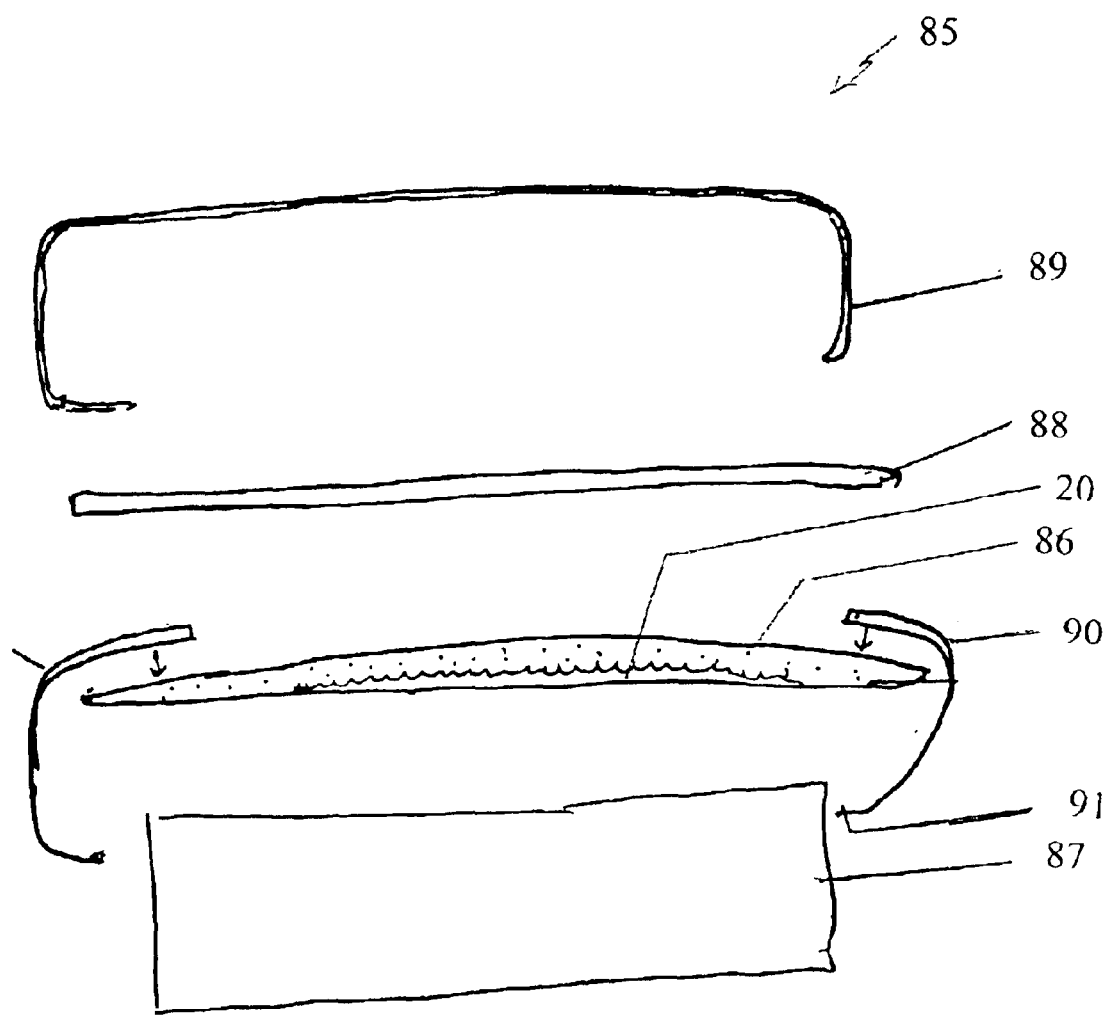
FIG. 10 is an exploded side view of a seat cushion support surface according to the present invention.

Turning to FIGS. 9 and 10, a preferred embodiment of a seat cushion support surface 85 includes a generally square-shaped bladder 86 surrounded on three sides (87a) and underneath (87b) by one or more firm foam-like support blocks 87, as shown in FIG. 9. The foam support block 87 surrounds and supports the backside of a user sitting on the seat cushion 85. The bladder 86 holds a liquid refrigerant 20, as described above (see FIG. 10). The seat cushion bladder 86 operates to cool the backside of the user sitting on it.

As shown in FIG. 10, the seat cushion support surface 85 also includes a soft cushioning material 88 on top of the bladder 86 for seating comfort, and ticking or another seat cushion cover material 89 covering the top of the seat cushion support surface 85. The soft cushioning material 88 is most preferably a low ILD (less than about 30 pounds) foam, or gel in a urethane envelope. ILD is an abbreviation for indentor load deflection, which is a measure of foam rigidity.

Finally, the seat cushion support surface 85 includes the conductive end portions 90 extending from two opposite sides of the bladder, as shown in FIG. 10. The ends of the conductive end portions 90 preferably overlap the upper wall of the bladder 86 by an inch or two, as shown in FIG. 10. These ends of the conductive end portions are preferably glued to the upper wall of the bladder using a suitable adhesive. The opposite ends of the conductive end portions 90 extend under the lower foam support block 87b.

Figure 11:
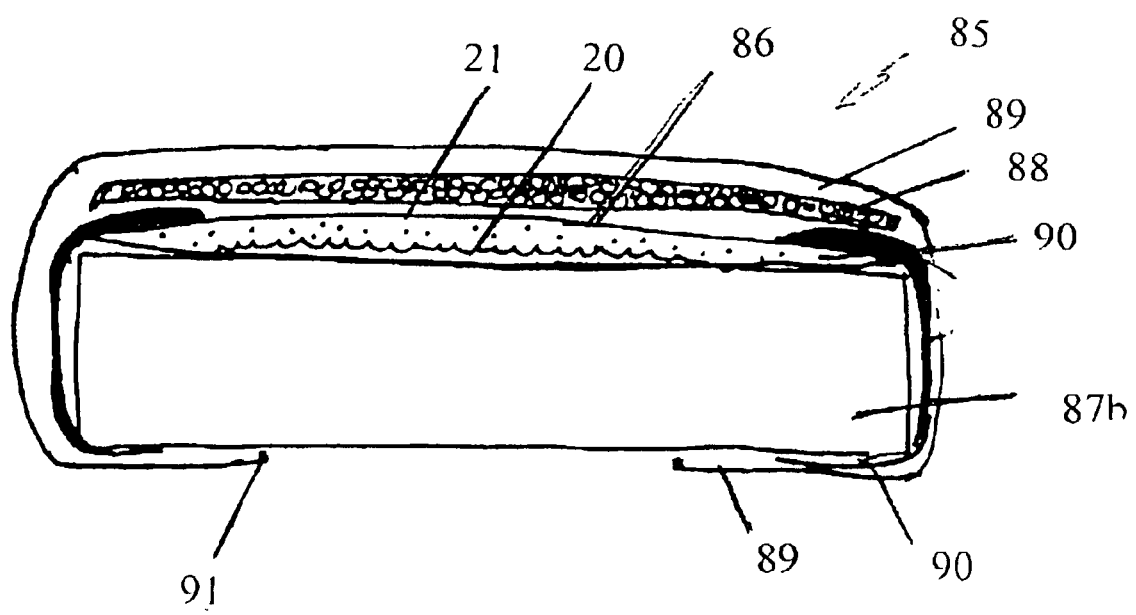
FIG. 11 is a cross-sectional view of a seat cushion support surface cover according to the present invention.

FIG. 11 shows a cross-section of an assembled seat cushion support surface 85, with a upper layer of ticking or seat cushion cover material 89 over a second layer of the soft, low ILD (indentor load deflection) foam 88. The soft, low ILD foam 88 extends over the bladder 86, which contains the small quantity of refrigerant liquid 20 and gas 21 with a boiling point just below body temperature and above room temperature. The bladder 86 rests on the upper surface of the lower firm foam support block 87b. The conductive end portions 90 extend off two opposite (or three) sides of the bladder 86, with some overlap over the edges of the upper wall of the bladder. The free ends of the conductive end portions 90, which are preferably made of copper, wrap around and under the foam support block. Thus, one seat cushion support surface embodiment herein further includes a foam layer above the bladder having an ILD (indentor load deflection) of less than about 30 pounds (low ILD), and a foam support block having an ILD of more than about 30 pounds (high ILD) below the bladder.

The ticking or seat cushion cover material 89 extends around the conductive end portions under the seat cushion 85. There is preferably an elastic band 91 sewn into the edges of the ticking or seat cushion cover material 89, which serves to hold the ends of the conductive end portions 90 against the lower surface of the foam support block 87b. The ticking or seat cushion cover material 89 may be removable for washing.

Continuing with the embodiments shown in FIGS. 9 through 11, the seat cushion support surface 85 preferably fits in a wheelchair, or on a day bed. The seat cushion support surface 85 is more comfortable than a conventional cushion, since it keeps the user's skin cooler than a conventional seat cushion. The upper surface of the seat cushion can be contoured for added comfort. Also, a patient bound to a wheelchair or day bed is less likely to develop bedsores. Keeping the skin cool and free of excess perspiration is helpful in avoiding bedsore formation. If the user does develop a decubitus ulcer on his or her bottom, the ulcer is less likely to worsen if the occupant uses a cooling seat cushion according to the present invention. The seat cushion can alternatively be a dog bed which would be helpful, for example, for a sick, or aging, infirm dog.

When a person sits on the seat cushion support surface 85, the central bladder 86 heats up, which causes the refrigerant liquid 20 in the bladder to move to the gaseous state. The gas 21, or vapor, rises to the cooler, higher ends of the bladder, where it condenses and flows by gravity back to the central part of the bladder, which is at a lower level than the ends of the bladder because the user is sitting on it. The warming/cooling cycle repeats itself within the bladder 86. Meanwhile, small amounts of heat are being distributed out onto the conductive pathways 90, where the heat dissipates. This results in a seat cushion that is cool and comfortable.

Figure 12:
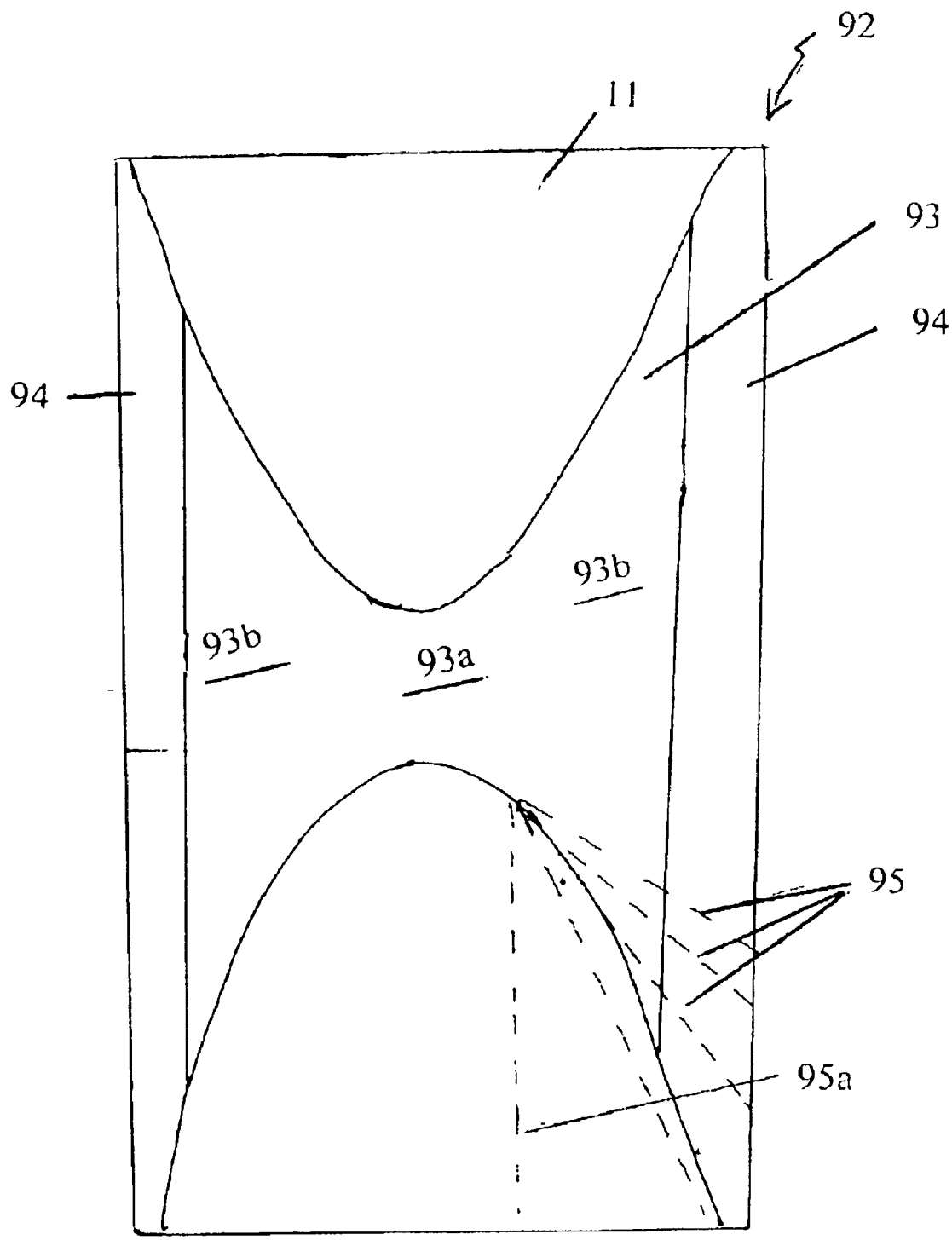
FIG. 12 is a top plan view of a support surface pad according to the present invention, showing various possible bladder shapes.

FIG. 12 shows an embodiment 92 of a mattress pad support surface. Here, the bladder 93 is generally bat wing-shaped, with relatively wide conductive end portions 94 adhered to opposite ends of the bladder 93. The opposite ends of the conductive end portions 94 extend down the sides of the mattress 11 and under it. The dashed lines 95 in FIG. 12 indicate a variety of possible bladder shapes. It has been found herein that a bladder with a narrower central portion 93a and wider ends 93b, as shown in FIG. 12, is optimal for distributing the user's body heat away from the user to the ends of the bladder 93 (via the action of the refrigerant), where it is conducted away to the conductive end portions 94. The heat dissipates to the ambient air from the conductive end portions 94. The parts of the user in contact with the support surface are thus kept cooler.

The bladder 93 can be customized by increasing the width of the bladder ends 93b for a larger heat exhaust area. For example, a bladder 93 with a shape indicated by dashed line 95a in FIG. 12 has a higher surface area and is suited for use by very large patients. In an alternate embodiment, a support surface pad resembling the support surface shown in FIG. 12 is incorporated into a mattress just under the mattress ticking.

Figure 13:
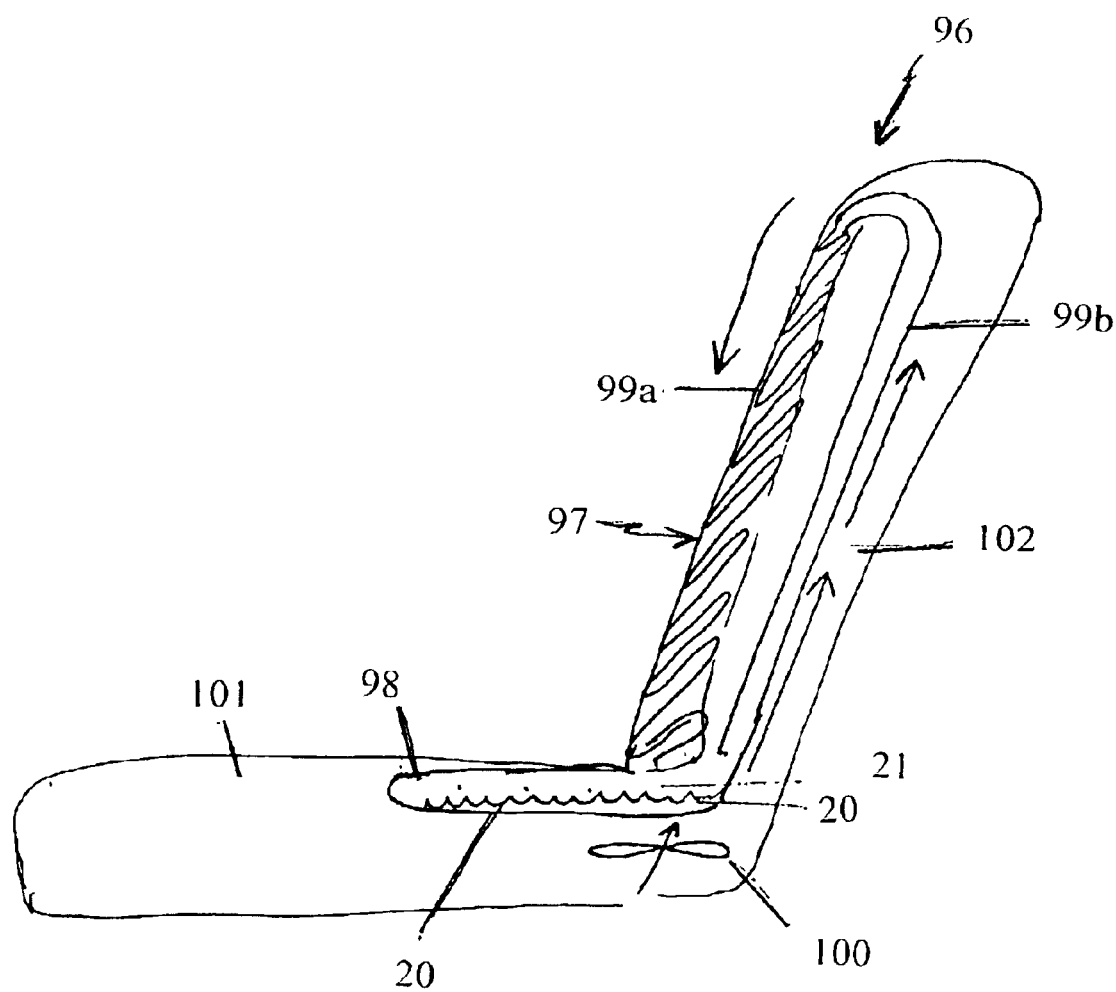
FIG. 13 is a side schematic view of a car seat support surface according to the present invention.
Figure 14:
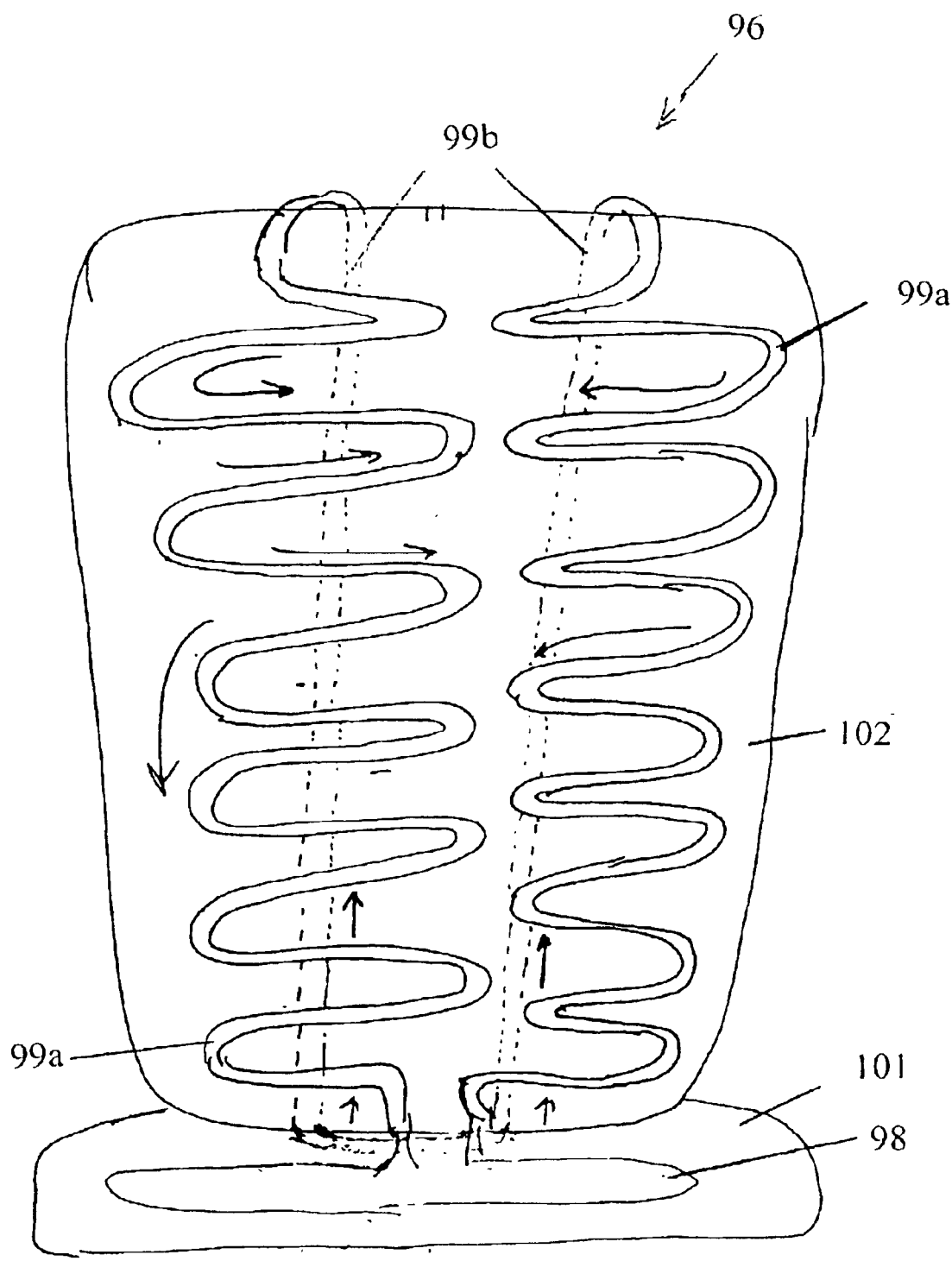
FIG. 14 is a top plan view of a car seat support surface according to the present invention.

FIGS. 13 and 14 show a preferred embodiment of a car seat support surface 96 with a trickle-down bladder system 97. The trickle-down bladder system 97 includes a seat bladder 98 containing liquid refrigerant 20 as described hereinabove, flexible trickle-down tubing 99 connected at both ends to the seat bladder 98, and a simple pump 100. The pump 100 is preferably built into the base 101 of the car seat under the bladder. Within the car seat back 102, the tubing 99 loops up the rear portion of the seat back, curves forward, and extends down a front portion of the seat back 102, as shown in FIGS. 13 and 14. Preferably, the rear section of tubing 99b is straight, and the front section of tubing 99a is coiled in a serpentine pattern. Each car seat support surface 96 preferably includes two side by side lengths of tubing 99, which are equal in size and length, as shown in FIG. 14.

The pump 100 operates to pump the liquid refrigerant through the rear section of the trickle-down tubing 99b back up to the top of the car seat back. The refrigerant 20 then trickles down the serpentine front section of tubing 99a by gravity back into the seat bladder 98, in the direction of the arrows shown in FIGS. 13 and 14. As the refrigerant 20 flows down the serpentine tubing 99a in the front section of the car seat back 102, heat from the user's back brings a certain percent of the refrigerant to boiling. This refrigerant then forms a gas 21 within the tubing. This has a cooling effect on the user/s back. Meanwhile, the refrigerant 20 in the seat bladder 98 is being heated by the user's bottom and cycling through the warming/cooling cycle within the bladder, resulting in heat dissipation. Rather than capturing body heat and delivering it back to the user's back as a conventional car seat may do, the support surface is effectively and comfortably wicking heat away from the user's back and bottom. This embodiment does not require conductive end portions, though short conductive end portions that are attached to the seat bladder may be included.

This embodiment is particularly well-suited for use in taxis, jets, helicopters, and other vehicles for long-distance travel. In a jet or helicopter, for example, the pilot (and navigator) may be suited up in a special jumpsuit for protection during possible fire or ejection. The pilot is often under stress and is uncomfortably hot and sweaty. Seat support surfaces according to the present invention can help to keep the pilot cool, thus improving his or her performance. In a taxi, the vehicle's doors are frequently being opened and closed and the air conditioner is not always effective, especially in the summertime. A driver's seat support surface according to the present invention can help to keep the driver cool and comfortable. These seat support surfaces can also be used for comfortable long-term passenger seating in trains, automobiles, planes, and for office workers.

In an alternate embodiment, a thin surface support seat pad with the appearance of the pad shown in FIG. 3 can be used on a conventional upholstered truck or taxi driver's seat to inhibit the skin on the driver's back and backside from heating up and sweating during a long drive. The support pad keeps the driver's back cooler than it would have been without the pad, and is more comfortable and effective than some other attempts at accomplishing this task, such as lambs' wool or wooden ball seat covers. This thin support surface pad could, of course, be used on other types of seats as well. The present invention maintains its cooling effect for a time below the "perspiration threshold" of about 32 to 34 degrees Centigrade, the temperature above which the skin perspiration rate increases markedly.

In an alternate embodiment, a cooling car seat pad includes two rectangular-shaped bladders connected to one another by fabric. Strips of thin, soft, folded copper conductive pathways extend from three sides of each bladder. The copper conductive pathways extend around the sides to the back of a conventional car seat. A strip of elastic is adhered to the outer edges of the flexible copper conductive pathways to removably hold the car seat pad onto the car seat.

Figure 15:
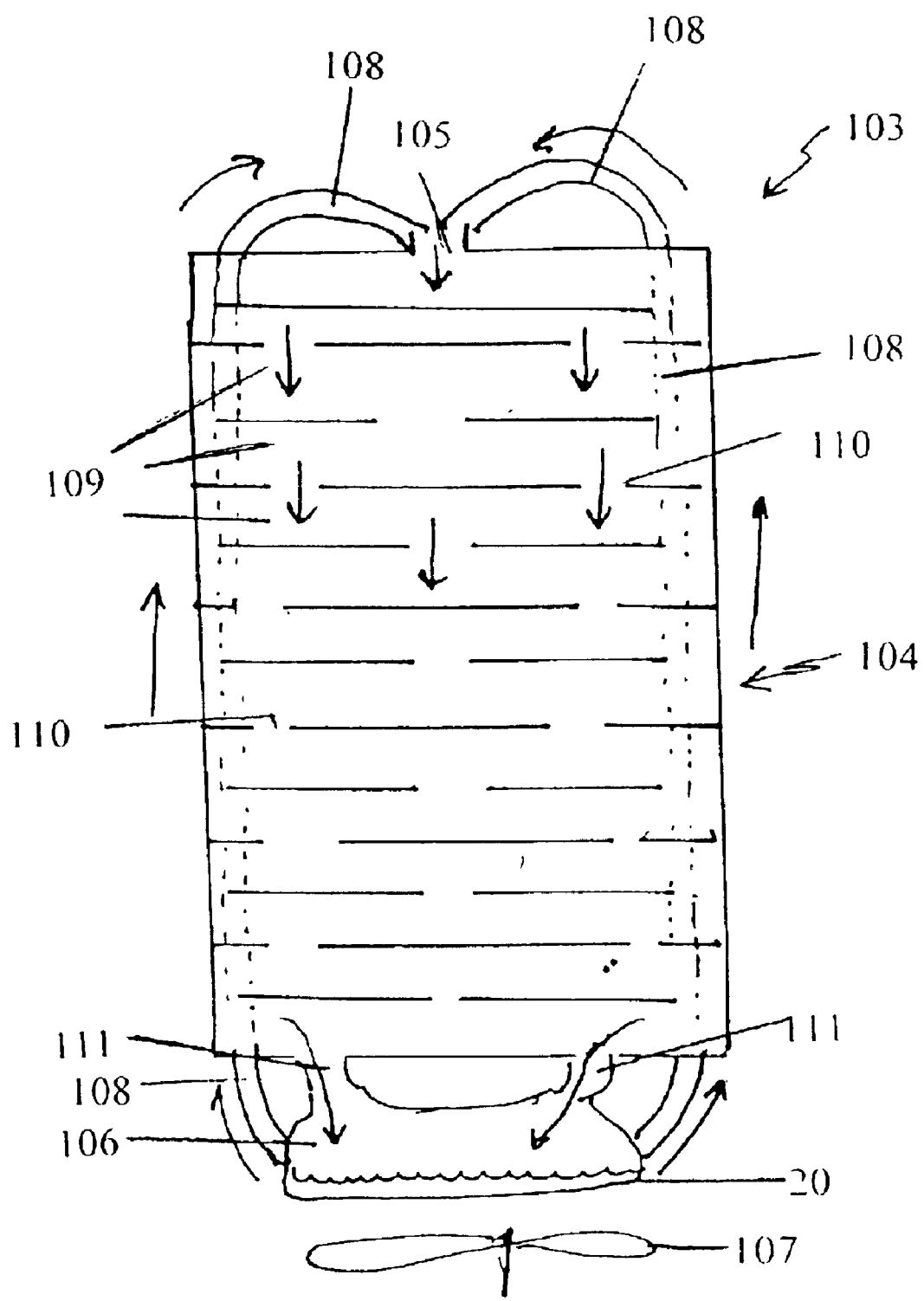
FIG. 15 is a top plan view of a car seat support surface pad according to the present invention.

Turning to FIG. 15, an alternate embodiment of a vehicle seat support surface 103 includes a main body 104 made of two same-sized, generally rectangular shaped sheets of a durable, flexible, gas-impermeable material that is strong enough to contain the refrigerant 20 and withstand liquid to gas cycling over time. The sheets are heat sealed to one another along their edges, with openings 105, 111 at the top (105) and bottom (111) of the main body. The vehicle seat support surface also includes a bladder 106 below the main body 104, and a pump 107 below the bladder 106. The pump 107 operates to pump liquid refrigerant 20 from the bladder 106 up a set of twin rear tubes 108 and into the central upper opening 105 at the top of the main body, in the direction of the arrows shown in FIG. 15. The main body 104 is heat welded to form parallel channels 109, as shown in FIG. 15. The channels 109 have staggered openings 110 (where the sheets have not been welded), though, so the liquid refrigerant 20 can trickle down through the channel openings 110 (between the two main body sheets) to the channel below. (The main body 104 with its channels 109 resembles a maze.) The main body 104 is in or on a back of the seat. At the bottom of the main body 104, the refrigerant 20 trickles into the bladder 106 through two matched lower openings 111 in the main body, as indicated by the arrows in FIG. 15, and the cycle continues as the liquid refrigerant 20 is pumped back up the rear tubes 108. In an alternate embodiment, the channels are serpentine in shape, rather than being straight and parallel as shown in FIG. 15.

As described hereinabove, in use, heat from the user's back heats up the vehicle seat bladder 106. As the refrigerant 20 boils, it forms a gas 21, which cools again as it moves to the edges of the main body 104. This cycle has the desirable effect of cooling the user's skin. This vehicle seat support surface 103 can be used on or in a seat of a car, plane, train, or other vehicle, or on or in any type of seat where cooling is desired.

From the foregoing it can be realized that the described device of the present invention may be easily and conveniently utilized as a therapeutic support surface. It is to be understood that any dimensions given herein are illustrative, and are not meant to be limiting.

While preferred embodiments of the invention have been described using specific terms, this description is for illustrative purposes only. It will be apparent to those of ordinary skill in the art that various modifications, substitutions, omissions, and changes may be made without departing from the spirit or scope of the invention, and that such are intended to be within the scope of the present invention as defined by the following claims. It is intended that the doctrine of equivalents be relied upon to determine the fair scope of these claims in connection with any other person's product which fall outside the literal wording of these claims, but which in reality do not materially depart from this invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

BRIEF LIST OF REFERENCE NUMBERS USED IN THE DRAWINGS 10 support surface
11 mattress
12 support surface mattress pad
13 central portion
14 pad conductive end portions
15 patient
16 pad bladder
16a upper bladder wall
16b lower bladder wall
17 ends of pad bladder
18 pad ticking
19 foam upper layer
20 refrigerant liquid
21 refrigerant vapor
22 net
23 first net strands
24 net cross-strands
25 conductive pathways
26 flexible non-conductive layer
27 metal sheet
28 lock and loop strips
29 free end of end portion
30 fold lines
32 upper side edge of mattress
33 upper side edge of mattress
34 warm zone
35 cool zone
36 free ends of pathways
40 dual bladder support surface system
41 first bladder of dual bladder embodiment
42 second bladder of dual bladder embodiment
43 ends of bladders
44 top edge of first bladder
45 bottom edge of first bladder
46 conductive end portions of dual bladder embodiment
47 conductive pathways of dual bladder embodiment
48 flexible non-conductive layer of dual bladder embodiment
50 external cooling system
51 cooling system tubing
52 cooling lantern
53 hospital bed
54 IV stand
55 arm of IV stand
56 handle of lantern
57 fan
58 plug
59 hollow center of lantern
60 open upper end of lantern
61 interior side wall
62 exterior side wall
63 refrigerant in lantern
64 droplets of refrigerant
65 interior space in lantern
67 coiled cooling tube
68 bladder end of tube
69 pressure relief valve
70 cylindrical cooling system
71 cooling cylinder
72 mattress bladder
73 support surface mattress
74 cylinder support
75 support arms
76 bladder tubing
77 electrical pump
78 support platform
79 lower end of cylinder
80 higher end of cylinder
81 electrical plug/wire
82 attached fan
85 seat cushion support surface
86 seat cushion bladder
87 firm foam support blocks
88 soft cushioning material
89 cushion cover material
90 cushion conductive pathways
91 elastic band in ticking
92 bat wing mattress pad support surface
93 bat wing-shaped bladder
93a central part of bat wing bladder
93b ends of bat wing bladder
94 bat wing conductive end portions
95 dashed lines—FIG. 12
96 car seat support surface
97 trickle-down bladder system
98 seat bladder
99a front section of trickle-down tubing
99b rear section of trickle-down tubing
100 car seat pump
101 base of car seat
102 car seat back
103 vehicle seat support surface
104 main body
105 central upper opening in main body
106 vehicle seat bladder
107 pump
108 rear tubes
109 channels
110 channel openings
111 lower openings in main body

What is claimed is:

1. A therapeutic support surface for patient comfort, maintaining a cool skin temperature, or reducing the incidence and promoting the healing of bedsores, the support surface comprising:

(a) a central portion comprising a hollow, enclosed bladder containing a pre-determined amount of liquid refrigerant, the refrigerant having a boiling point between about 23 and about 35 degrees Centigrade;

(b) a flexible spacer mechanism contained in the bladder, the spacer mechanism separating an upper bladder wall from a lower bladder wall; and (c) conductive end portions attached to opposite ends of the bladder, the conductive end portions comprising a flexible heat conductive material layer.

2. The support surface according to claim 1, wherein the heat conductive layer comprises same-sized, generally rectangular-shaped conductive strips of a metal sheet material.

3. The support surface according to claim 1, wherein the bladder is generally bow tie or butterfly shaped, with longer, matching ends and a narrower center.

4. The support surface according to claim 1, wherein the spacer mechanism is a floating net, which lies substantially parallel to the upper and lower walls of the bladder.

5. The support surface according to claim 4, the central portion further comprising an upper foam, gel, or enclosed silicone fluid layer.

6. The support surface according to claim 4, wherein the refrigerant forms a vapor when it is above its boiling point.

7. The support surface according to claim 4, wherein the refrigerant has a boiling point between about 23 and 35 degrees Centigrade.

8. The support surface according to claim 6, wherein the net is comprised of a plurality of first strands connected to a plurality of second, cross strands, the first strands being parallel to one another.

9. The support surface according to claim 8, wherein the second, cross strands of the net are generally parallel to one another and overlay the first net strands, forming openings between the strands.

10. The support surface according to claim 9, wherein the refrigerant has a boiling point between about 80 and 85 degrees Fahrenheit.

11. The support surface according to claim 2, wherein the conductive strips are connected to one another side by side, and the metal is copper or aluminum.

12. The support surface according to claim 2, wherein the conductive end portions further comprise a flexible, non-conductive lower layer, a lower face of a plurality of the conductive strips being attached to the flexible, non-conductive lower layer.

13. The support surface according to claim 12, wherein the refrigerant is a mixture comprising from about 5 to 50 weight % of 1,1,1,3,3-pentafluoropropane, and from about 50 to 95 weight % of a fluorochemical liquid.

14. The support surface according to claim 1, wherein the bladder is generally "H" shaped.

15. The support surface according to claim 14, the central portion further comprising a cover layer of ticking material.

16. The support surface according to claim 1, wherein the support surface is a seat cushion or seat back, and the bladder is generally rectangular-shaped.

17. The support surface according to claim 13, wherein the support surface is a child seat.

18. The support surface according to claim 1, further comprising two matching, enclosed second bladders; each second bladder substantially overlapping an end section of the first bladder; the first bladder containing refrigerant with a boiling point between about 83 and 90 degrees Fahrenheit; the second bladders containing a refrigerant liquid with a lower boiling point than the refrigerant in the bladder.

19. The support surface according to claim 18, wherein the second bladders are elevated above the plane of the first bladder; each second bladder being connected along one of its ends to a conductive end portion.

20. The support surface according to claim 19, wherein each conductive end portion comprises a plurality of conductive strip pathways, each conductive strip pathway being attached on its bottom face to a flexible, non-conductive material.

21. The support surface according to claim 1, further comprising an external cooling system attached by tubing to the bladder.

22. The support surface according to claim 21, wherein the external cooling system comprises a high surface area heat dissipation device, and a fan at the base of the heat dissipation device, the heat dissipation device comprising a cavity for containing the refrigerant.

23. The support surface according to claim 22, wherein the heat dissipation device is a lantern-shaped cooling device comprising a hollow center and parallel, circular interior and exterior walls defining a space, the space holding the liquid refrigerant.

24. The support surface according to claim 1, further comprising an external cooling system, which comprises a coiled cooling tube, one end of the coiled cooling tube being removably attachable to a fitting in a wall of the bladder, the opposite end of the coiled cooling tube comprising a pressure relief valve for releasing pressure in the coiled cooling tube.

25. The support surface according to claim 1, further comprising an external cooling system, which comprises a cooling cylinder, operable pump, and tubing, the tubing connecting the bladder to the cooling cylinder, a lower, posterior end of the cooling cylinder being below the level of its opposite, upper, anterior end; wherein the pump is operable to pump refrigerant through the tubing back up to the bladder.

26. The support surface according to claim 1, wherein the cooling cylinder is mounted on a cylinder support under a frame supporting the support surface, the cylinder support being connectable to the frame.

27. The support surface according to claim 5, further comprising a foam layer above the bladder having an ILD (indentor load deflection) of less than about 30 pounds, and a foam support block having an ILD of more than about 30 pounds below the bladder; wherein an end portion of the conductive end portions extend down opposite sides of the foam support block and under it, and wherein the support surface is a seat cushion.

* * * * *